(12) United States Patent
Telfort et al.

(10) Patent No.: US 10,441,181 B1
(45) Date of Patent: Oct. 15, 2019

(54) ACOUSTIC PULSE AND RESPIRATION MONITORING SYSTEM

(71) Applicant: MASIMO CORPORATION, Irvine, CA (US)

(72) Inventors: Valery G. Telfort, Laval (CA); Rouzbeh Khatibi, Saint-Laurent (CA)

(73) Assignee: Masimo Corporation, Irvine, CA (US)

( * ) Notice: Subject to any disclaimer, the term of this patent is extended or adjusted under 35 U.S.C. 154(b) by 252 days.

(21) Appl. No.: 14/636,500

(22) Filed: Mar. 3, 2015

Related U.S. Application Data

(63) Continuation of application No. 14/206,900, filed on Mar. 12, 2014.

(60) Provisional application No. 61/780,412, filed on Mar. 13, 2013.

(51) Int. Cl.
  *A61B 5/0245* (2006.01)
  *A61B 5/00* (2006.01)
  *A61B 5/0295* (2006.01)

(52) U.S. Cl.
  CPC ........ *A61B 5/02455* (2013.01); *A61B 5/0295* (2013.01); *A61B 5/6822* (2013.01); *A61B 5/7278* (2013.01); *A61B 5/746* (2013.01)

(58) Field of Classification Search
  CPC . A61B 5/02455; A61B 5/0295; A61B 5/6822; A61B 5/746; A61B 5/7278
  See application file for complete search history.

(56) References Cited

U.S. PATENT DOCUMENTS

| | | |
|---|---|---|
| 3,682,161 A | 8/1972 | Alibert |
| 4,127,749 A | 11/1978 | Atoji et al. |
| 4,326,143 A | 4/1982 | Guth et al. |
| 4,507,653 A | 3/1985 | Bayer |
| 4,537,200 A | 8/1985 | Widrow |

(Continued)

FOREIGN PATENT DOCUMENTS

| | | |
|---|---|---|
| CA | 2262236 | 4/2008 |
| EP | 0716628 | 12/1998 |

(Continued)

OTHER PUBLICATIONS

US 8,845,543 B2, 09/2014, Diab et al. (withdrawn)

(Continued)

*Primary Examiner* — Jacqueline Cheng
*Assistant Examiner* — Tho Q Tran
(74) *Attorney, Agent, or Firm* — Knobbe, Martens, Olson & Bear, LLP

(57) ABSTRACT

An acoustic sensor attached to a medical patient can noninvasively detect acoustic vibrations indicative of physiological parameters of the medical patient and produce an acoustic signal corresponding to the acoustic vibrations. The acoustic signal can be integrated one or more times with respect to time, and a physiological monitoring system can determine pulse or respiration parameters based on the integrated acoustic signal. The physiological monitoring system can, for instance, estimate a pulse rate according to pulses in the integrated acoustic signal and a respiration rate according to a modulation of the integrated acoustic signal, among other parameters. Further, the physiological monitoring system can compare the integrated acoustic signal or parameters determined based on the integrated acoustic signal with other signals or parameters to activate alarms.

20 Claims, 14 Drawing Sheets

(56) References Cited

U.S. PATENT DOCUMENTS

| | | | |
|---|---|---|---|
| 4,685,140 | A * | 8/1987 | Mount, II ................. G06T 7/00 351/212 |
| 4,714,341 | A | 12/1987 | Hamaguri |
| 4,848,901 | A | 7/1989 | Hood, Jr. |
| 4,884,809 | A | 12/1989 | Rowan |
| 4,958,638 | A | 9/1990 | Sharpe et al. |
| 4,960,128 | A | 10/1990 | Gordon et al. |
| 4,964,408 | A | 10/1990 | Hink et al. |
| 5,033,032 | A | 7/1991 | Houghtaling |
| 5,041,187 | A | 8/1991 | Hink et al. |
| 5,069,213 | A | 12/1991 | Polczynski |
| 5,143,078 | A | 9/1992 | Mather et al. |
| 5,163,438 | A | 11/1992 | Gordon et al. |
| 5,309,922 | A | 5/1994 | Schechter et al. |
| 5,319,355 | A | 6/1994 | Russek |
| 5,337,744 | A | 8/1994 | Branigan |
| 5,341,805 | A | 8/1994 | Stavridi et al. |
| 5,353,798 | A * | 10/1994 | Sieben ..................... A61B 8/12 128/925 |
| D353,195 | S | 12/1994 | Savage et al. |
| D353,196 | S | 12/1994 | Savage et al. |
| 5,377,302 | A | 12/1994 | Tsiang |
| 5,377,676 | A | 1/1995 | Vari et al. |
| D359,546 | S | 6/1995 | Savage et al. |
| 5,431,170 | A | 7/1995 | Mathews |
| D361,840 | S | 8/1995 | Savage et al. |
| D362,063 | S | 9/1995 | Savage et al. |
| 5,448,996 | A | 9/1995 | Bellin et al. |
| 5,452,717 | A | 9/1995 | Branigan et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,561,275 | A | 10/1996 | Savage et al. |
| 5,562,002 | A | 10/1996 | Lalin |
| 5,590,649 | A | 1/1997 | Caro et al. |
| 5,602,924 | A | 2/1997 | Durand et al. |
| 5,632,272 | A | 5/1997 | Diab et al. |
| 5,638,403 | A | 6/1997 | Birchler et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,191 | A | 9/1997 | Gerdt |
| 5,685,299 | A | 11/1997 | Diab et al. |
| 5,724,983 | A | 3/1998 | Selker et al. |
| D393,830 | S | 4/1998 | Tobler et al. |
| 5,743,262 | A | 4/1998 | Lepper, Jr. et al. |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,819,007 | A | 10/1998 | Elghazzawi |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,865,736 | A | 2/1999 | Baker, Jr. et al. |
| 5,890,929 | A | 4/1999 | Mills et al. |
| 5,904,654 | A | 5/1999 | Wohltmann et al. |
| 5,919,134 | A | 7/1999 | Diab |
| 5,928,156 | A | 7/1999 | Krumbiegel |
| 5,934,925 | A | 8/1999 | Tobler et al. |
| 5,940,182 | A | 8/1999 | Lepper, Jr. et al. |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,027,452 | A | 2/2000 | Flaherty et al. |
| 6,029,665 | A | 2/2000 | Berthon-Jones |
| 6,036,642 | A | 3/2000 | Diab et al. |
| 6,045,509 | A | 4/2000 | Caro et al. |
| 6,064,910 | A | 5/2000 | Andersson et al. |
| 6,067,462 | A | 5/2000 | Diab et al. |
| 6,081,735 | A | 6/2000 | Diab et al. |
| 6,083,172 | A | 7/2000 | Baker et al. |
| 6,088,607 | A | 7/2000 | Diab et al. |
| 6,110,522 | A | 8/2000 | Lepper, Jr. et al. |
| 6,112,171 | A | 8/2000 | Sugiyama et al. |
| 6,124,597 | A | 9/2000 | Shehada |
| 6,128,521 | A | 10/2000 | Marro et al. |
| 6,129,675 | A | 10/2000 | Jay |
| 6,138,675 | A | 10/2000 | Berthon-Jones |
| 6,139,505 | A | 10/2000 | Murphy |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,168,568 | B1 | 1/2001 | Gavriely |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,248,083 | B1 | 6/2001 | Smith et al. |
| 6,253,097 | B1 | 6/2001 | Aronow et al. |
| 6,254,551 | B1 | 7/2001 | Varis |
| 6,256,523 | B1 | 7/2001 | Diab et al. |
| 6,261,238 | B1 | 7/2001 | Gavriely |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,301,493 | B1 | 10/2001 | Marro et al. |
| 6,317,627 | B1 | 11/2001 | Ennen et al. |
| 6,321,100 | B1 | 11/2001 | Parker |
| 6,325,761 | B1 | 12/2001 | Jay |
| 6,331,162 | B1 | 12/2001 | Mitchell |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,383,143 | B1 | 5/2002 | Rost |
| 6,388,240 | B2 | 5/2002 | Schulz et al. |
| 6,397,091 | B2 | 5/2002 | Diab et al. |
| 6,430,437 | B1 | 8/2002 | Marro |
| 6,430,525 | B1 | 8/2002 | Weber et al. |
| 6,443,907 | B1 | 9/2002 | Mansy et al. |
| 6,463,311 | B1 | 10/2002 | Diab |
| 6,470,199 | B1 | 10/2002 | Kopotic et al. |
| 6,486,588 | B2 | 11/2002 | Doron et al. |
| 6,491,647 | B1 | 12/2002 | Bridger et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,517,497 | B2 | 2/2003 | Rymut et al. |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,647,280 | B2 | 11/2003 | Bahr et al. |
| 6,650,917 | B2 | 11/2003 | Diab et al. |

(56) References Cited

U.S. PATENT DOCUMENTS

| | | |
|---|---|---|
| 6,654,624 B2 | 11/2003 | Diab et al. |
| 6,658,276 B2 | 12/2003 | Kiani et al. |
| 6,659,960 B2 | 12/2003 | Derksen et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,074 B1 | 4/2004 | Kastle |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,754,516 B2 | 6/2004 | Mannheimer |
| 6,760,607 B2 | 7/2004 | Al-Ali |
| 6,766,038 B1 | 7/2004 | Sakuma et al. |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,839,581 B1 | 1/2005 | Ei-Solh et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,096,060 B2 | 8/2006 | Arand et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,194,306 B1 | 3/2007 | Turcott |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,267,652 B2 | 9/2007 | Coyle et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,361,146 B1 | 4/2008 | Bharmi et al. |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,398,115 B2 | 7/2008 | Lynn |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,539,533 B2 | 5/2009 | Tran |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,690,378 B1 | 4/2010 | Turcott |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |

(56) References Cited

U.S. PATENT DOCUMENTS

| | | | |
|---|---|---|---|
| 7,844,314 | B2 | 11/2010 | Al-Ali |
| 7,844,315 | B2 | 11/2010 | Al-Ali |
| 7,865,222 | B2 | 1/2011 | Weber et al. |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,899,518 | B2 | 3/2011 | Trepagnier et al. |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,937,130 | B2 | 5/2011 | Diab et al. |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |
| 7,988,637 | B2 | 8/2011 | Diab |
| 7,990,382 | B2 | 8/2011 | Kiani |
| 7,991,446 | B2 | 8/2011 | Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,727 | B2 | 10/2011 | Schurman et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| RE43,169 | E | 2/2012 | Parker |
| 8,118,620 | B2 | 2/2012 | Al-Ali et al. |
| 8,126,528 | B2 | 2/2012 | Diab et al. |
| 8,128,572 | B2 | 3/2012 | Diab et al. |
| 8,130,105 | B2 | 3/2012 | Al-Ali et al. |
| 8,145,287 | B2 | 3/2012 | Diab et al. |
| 8,150,487 | B2 | 4/2012 | Diab et al. |
| 8,175,672 | B2 | 5/2012 | Parker |
| 8,180,420 | B2 | 5/2012 | Diab et al. |
| 8,182,443 | B1 | 5/2012 | Kiani |
| 8,185,180 | B2 | 5/2012 | Diab et al. |
| 8,190,223 | B2 | 5/2012 | Al-Ali et al. |
| 8,190,227 | B2 | 5/2012 | Diab et al. |
| 8,203,438 | B2 | 6/2012 | Kiani et al. |
| 8,203,704 | B2 | 6/2012 | Merritt et al. |
| 8,204,566 | B2 | 6/2012 | Schurman et al. |
| 8,219,172 | B2 | 7/2012 | Schurman et al. |
| 8,224,411 | B2 | 7/2012 | Al-Ali et al. |
| 8,228,181 | B2 | 7/2012 | Al-Ali |
| 8,229,533 | B2 | 7/2012 | Diab et al. |
| 8,233,955 | B2 | 7/2012 | Al-Ali et al. |
| 8,244,325 | B2 | 8/2012 | Al-Ali et al. |
| 8,255,026 | B1 | 8/2012 | Al-Ali |
| 8,255,027 | B2 | 8/2012 | Al-Ali et al. |
| 8,255,028 | B2 | 8/2012 | Al-Ali et al. |
| 8,260,577 | B2 | 9/2012 | Weber et al. |
| 8,265,723 | B1 | 9/2012 | McHale et al. |
| 8,274,360 | B2 | 9/2012 | Sampath et al. |
| 8,301,217 | B2 | 10/2012 | Al-Ali et al. |
| 8,306,596 | B2 | 11/2012 | Schurman et al. |
| 8,310,336 | B2 | 11/2012 | Muhsin et al. |
| 8,315,683 | B2 | 11/2012 | Al-Ali et al. |
| RE43,860 | E | 12/2012 | Parker |
| 8,337,403 | B2 | 12/2012 | Al-Ali et al. |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,359,080 | B2 | 1/2013 | Diab et al. |
| 8,364,223 | B2 | 1/2013 | Al-Ali et al. |
| 8,364,226 | B2 | 1/2013 | Diab et al. |
| 8,374,665 | B2 | 2/2013 | Lamego |
| 8,385,995 | B2 | 2/2013 | Al-ali et al. |
| 8,385,996 | B2 | 2/2013 | Smith et al. |
| 8,388,353 | B2 | 3/2013 | Kiani et al. |
| 8,399,822 | B2 | 3/2013 | Al-Ali |
| 8,401,602 | B2 | 3/2013 | Kiani |
| 8,405,608 | B2 | 3/2013 | Al-Ali et al. |
| 8,414,499 | B2 | 4/2013 | Al-Ali et al. |
| 8,418,524 | B2 | 4/2013 | Al-Ali |
| 8,423,106 | B2 | 4/2013 | Lamego et al. |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,455,290 | B2 | 6/2013 | Siskavich |
| 8,457,703 | B2 | 6/2013 | Al-Ali |
| 8,457,707 | B2 | 6/2013 | Kiani |
| 8,463,349 | B2 | 6/2013 | Diab et al. |
| 8,466,286 | B2 | 6/2013 | Bellot et al. |
| 8,471,713 | B2 | 6/2013 | Poeze et al. |
| 8,473,020 | B2 | 6/2013 | Kiani et al. |
| 8,478,538 | B2 | 7/2013 | McGonigle et al. |
| 8,483,787 | B2 | 7/2013 | Al-Ali et al. |
| 8,489,364 | B2 | 7/2013 | Weber et al. |
| 8,498,684 | B2 | 7/2013 | Weber et al. |
| 8,504,128 | B2 | 8/2013 | Blank et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,560,032 | B2 | 10/2013 | Al-Ali et al. |
| 8,560,034 | B1 | 10/2013 | Diab et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |
| 8,571,619 | B2 | 10/2013 | Al-Ali et al. |
| 8,584,345 | B2 | 10/2013 | Al-Ali et al. |
| 8,577,431 | B2 | 11/2013 | Lamego et al. |
| 8,581,732 | B2 | 11/2013 | Al-Ali et al. |
| 8,588,880 | B2 | 11/2013 | Abdul-Hafiz et al. |
| 8,597,274 | B2 | 12/2013 | Sloan |
| 8,600,467 | B2 | 12/2013 | Al-Ali et al. |
| 8,606,342 | B2 | 12/2013 | Diab |
| 8,622,902 | B2 | 1/2014 | Woehrle |
| 8,626,255 | B2 | 1/2014 | Al-Ali et al. |
| 8,630,691 | B2 | 1/2014 | Lamego et al. |
| 8,634,889 | B2 | 1/2014 | Al-Ali et al. |
| 8,641,631 | B2 | 2/2014 | Sierra et al. |
| 8,652,060 | B2 | 2/2014 | Al-Ali |
| 8,663,107 | B2 | 3/2014 | Kiani |
| 8,666,468 | B1 | 3/2014 | Al-Ali |
| 8,667,967 | B2 | 3/2014 | Al-Ali et al. |
| 8,670,811 | B2 | 3/2014 | O'Reilly |
| 8,670,814 | B2 | 3/2014 | Diab et al. |
| 8,676,286 | B2 | 3/2014 | Weber et al. |
| 8,682,407 | B2 | 3/2014 | Al-Ali |
| RE44,823 | E | 4/2014 | Parker |
| RE44,875 | E | 4/2014 | Kiani et al. |
| 8,690,799 | B2 | 4/2014 | Telfort et al. |
| 8,700,112 | B2 | 4/2014 | Kiani |
| 8,702,627 | B2 | 4/2014 | Telfort et al. |
| 8,706,179 | B2 | 4/2014 | Parker |
| 8,712,494 | B1 | 4/2014 | MacNeish, III et al. |
| 8,715,206 | B2 | 5/2014 | Telfort et al. |
| 8,718,735 | B2 | 5/2014 | Lamego et al. |
| 8,718,737 | B2 | 5/2014 | Diab et al. |
| 8,718,738 | B2 | 5/2014 | Blank et al. |
| 8,720,249 | B2 | 5/2014 | Al-Ali |

(56) References Cited

U.S. PATENT DOCUMENTS

| | | |
|---|---|---|
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,792,949 B2 | 7/2014 | Baker |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,135,398 B2 | 9/2015 | Kaib |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,220,440 B2 | 12/2015 | Addison et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 1/2016 | Abdul-Hafiz et al. |
| 9,267,572 B2 | 2/2016 | Barker et al. |
| 9,277,880 B2 | 2/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,378,637 B2 | 6/2016 | Kaib |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,693 B2 | 4/2017 | Diab |
| 9,659,475 B2 | 5/2017 | Kaib |
| 9,724,016 B1 | 8/2017 | Al-Ali et al. |
| 2001/0002206 A1 | 5/2001 | Diab et al. |
| 2002/0193670 A1 | 12/2002 | Garfield et al. |
| 2003/0015368 A1 | 1/2003 | Cybulski et al. |
| 2003/0065269 A1* | 4/2003 | Vetter ............... A61B 5/02416 600/503 |
| 2003/0076494 A1 | 4/2003 | Bonin et al. |
| 2003/0158466 A1 | 8/2003 | Lynn et al. |
| 2003/0163033 A1 | 8/2003 | Dekker |
| 2003/0163054 A1 | 8/2003 | Dekker |
| 2004/0010202 A1 | 1/2004 | Nakatani |
| 2004/0059203 A1 | 3/2004 | Guerrero |
| 2004/0060362 A1* | 4/2004 | Kjellmann ........... A61B 5/0215 73/754 |
| 2004/0133087 A1 | 7/2004 | Ali et al. |

(56) References Cited

U.S. PATENT DOCUMENTS

| | | |
|---|---|---|
| 2004/0158162 A1 | 8/2004 | Narimatsu |
| 2004/0225332 A1* | 11/2004 | Gebhardt ............ A61N 1/3622 607/17 |
| 2005/0027205 A1 | 2/2005 | Tarassenko et al. |
| 2005/0048456 A1 | 3/2005 | Chefd'hotel et al. |
| 2005/0070774 A1 | 3/2005 | Addison et al. |
| 2005/0107699 A1* | 5/2005 | Loftman ............ G01S 7/52026 600/437 |
| 2005/0116820 A1 | 6/2005 | Goldreich |
| 2005/0199056 A1* | 9/2005 | Strong ............... G01C 13/006 73/170.29 |
| 2006/0047215 A1 | 3/2006 | Newman et al. |
| 2006/0129216 A1* | 6/2006 | Hastings ............ A61B 5/0215 607/115 |
| 2006/0149144 A1 | 7/2006 | Lynn et al. |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0189880 A1 | 8/2006 | Lynn et al. |
| 2006/0195041 A1 | 8/2006 | Lynn et al. |
| 2006/0235324 A1 | 10/2006 | Lynn |
| 2006/0238333 A1 | 10/2006 | Welch et al. |
| 2006/0241510 A1 | 10/2006 | Halperin et al. |
| 2006/0258921 A1 | 11/2006 | Addison et al. |
| 2007/0093721 A1 | 4/2007 | Lynn et al. |
| 2007/0129643 A1 | 6/2007 | Kwok et al. |
| 2007/0129647 A1 | 6/2007 | Lynn |
| 2007/0135725 A1 | 6/2007 | Hatlestad |
| 2007/0149860 A1 | 6/2007 | Lynn et al. |
| 2007/0163353 A1* | 7/2007 | Lec ................... A61B 5/0215 73/700 |
| 2007/0185397 A1 | 8/2007 | Govari et al. |
| 2007/0239057 A1 | 10/2007 | Pu et al. |
| 2007/0282212 A1 | 12/2007 | Sierra et al. |
| 2008/0013747 A1 | 1/2008 | Tran |
| 2008/0039735 A1 | 2/2008 | Hickerson |
| 2008/0071185 A1 | 3/2008 | Beck et al. |
| 2008/0076972 A1 | 3/2008 | Dorogusker et al. |
| 2008/0119716 A1 | 5/2008 | Boric-Lubecke et al. |
| 2008/0161878 A1 | 7/2008 | Tehrani et al. |
| 2008/0177195 A1 | 7/2008 | Armitstead |
| 2008/0188733 A1 | 8/2008 | Al-Ali |
| 2008/0188760 A1 | 8/2008 | Al-Ali |
| 2008/0218153 A1 | 9/2008 | Patel et al. |
| 2008/0275349 A1 | 11/2008 | Halperin et al. |
| 2008/0304580 A1 | 12/2008 | Ichiyama |
| 2009/0018429 A1 | 1/2009 | Saliga et al. |
| 2009/0018453 A1 | 1/2009 | Banet et al. |
| 2009/0093687 A1* | 4/2009 | Telfort ................ A61B 5/0002 600/300 |
| 2009/0112096 A1 | 4/2009 | Tamura |
| 2009/0160654 A1* | 6/2009 | Yang ................... B29B 9/12 340/572.9 |
| 2009/0167332 A1* | 7/2009 | Forbes ............ G01R 1/06772 324/755.02 |
| 2009/0187065 A1 | 7/2009 | Basinger |
| 2009/0240119 A1 | 9/2009 | Schwaibold et al. |
| 2009/0247848 A1 | 10/2009 | Baker |
| 2009/0247984 A1 | 10/2009 | Lamego et al. |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0004552 A1 | 1/2010 | Zhang et al. |
| 2010/0016682 A1 | 1/2010 | Schluess et al. |
| 2010/0016693 A1 | 1/2010 | Addison |
| 2010/0030040 A1 | 2/2010 | Poeze et al. |
| 2010/0204550 A1 | 8/2010 | Heneghan |
| 2010/0261979 A1 | 10/2010 | Kiani |
| 2010/0274099 A1 | 10/2010 | Telfort et al. |
| 2010/0295686 A1 | 11/2010 | Sloan |
| 2010/0298661 A1 | 11/2010 | McCombie et al. |
| 2010/0298730 A1 | 11/2010 | Taressenko et al. |
| 2010/0324377 A1 | 12/2010 | Woehrle |
| 2011/0001605 A1 | 1/2011 | Kiani |
| 2011/0009710 A1 | 1/2011 | Kroeger et al. |
| 2011/0040713 A1 | 2/2011 | Colman |
| 2011/0074409 A1 | 3/2011 | Stoughton |
| 2011/0082711 A1 | 4/2011 | Poeze et al. |
| 2011/0105854 A1 | 5/2011 | Kiani et al. |
| 2011/0118573 A1 | 5/2011 | McKenna |
| 2011/0125060 A1 | 5/2011 | Telfort et al. |
| 2011/0172561 A1 | 7/2011 | Kiani et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0222371 A1* | 9/2011 | Liu ..................... G01V 13/00 367/76 |
| 2011/0230733 A1 | 9/2011 | Al-Ali et al. |
| 2011/0237911 A1 | 9/2011 | Lamego et al. |
| 2012/0016255 A1 | 1/2012 | Masuo |
| 2012/0059267 A1 | 3/2012 | Lamego et al. |
| 2012/0070013 A1* | 3/2012 | Vau ..................... G10K 11/178 381/71.4 |
| 2012/0101344 A1 | 4/2012 | Desjardins |
| 2012/0116175 A1 | 5/2012 | Al-Ali et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0253140 A1 | 10/2012 | Addison et al. |
| 2012/0262298 A1 | 10/2012 | Bohm |
| 2012/0283524 A1 | 11/2012 | Kiani et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0045685 A1 | 2/2013 | Kiani |
| 2013/0046204 A1 | 2/2013 | Lamego |
| 2013/0041591 A1 | 3/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0128690 A1* | 5/2013 | Gopalan ............ G01S 7/5205 367/7 |
| 2013/0162433 A1 | 6/2013 | Muhsin et al. |
| 2013/0190581 A1 | 7/2013 | Al-Ali et al. |
| 2013/0190595 A1* | 7/2013 | Oraevsky ............ A61B 5/0095 600/407 |
| 2013/0197328 A1 | 8/2013 | Diab et al. |
| 2013/0243021 A1 | 9/2013 | Siskavich |
| 2013/0253334 A1 | 9/2013 | Al-Ali et al. |
| 2013/0274571 A1 | 10/2013 | Diab et al. |
| 2013/0296672 A1 | 11/2013 | Dalvi et al. |
| 2013/0317370 A1 | 11/2013 | Dalvi et al. |
| 2013/0324808 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Lamego et al. |
| 2014/0025306 A1 | 1/2014 | Weber et al. |
| 2014/0034353 A1 | 2/2014 | Al-Ali et al. |
| 2014/0051953 A1 | 2/2014 | Lamego et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |

(56) References Cited

U.S. PATENT DOCUMENTS

| | | |
|---|---|---|
| 2014/0171763 A1 | 6/2014 | Diab |
| 2014/0180038 A1 | 6/2014 | Kiani et al. |
| 2014/0180154 A1 | 6/2014 | Sierra et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0206963 A1 | 7/2014 | Diab et al. |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

FOREIGN PATENT DOCUMENTS

| | | |
|---|---|---|
| EP | 0659058 | 1/1999 |
| EP | 1207536 | 5/2002 |
| GB | 2358546 | 11/1999 |
| JP | 6214898 | 1/1987 |
| JP | 01-309872 | 6/1998 |
| JP | 10-155755 | 6/1998 |
| JP | 2001-50713 | 5/1999 |
| JP | 2003-329719 | 11/2003 |
| WO | WO 1994/005207 | 3/1994 |
| WO | WO 1994/013207 | 6/1994 |
| WO | WO 1995/029632 | 11/1995 |
| WO | WO 1999/053277 | 10/1999 |
| WO | WO 2000/010462 | 3/2000 |
| WO | WO 2001/034033 | 5/2001 |
| WO | WO 2001/078059 | 10/2001 |
| WO | WO 2001/097691 | 12/2001 |
| WO | WO 2002/003042 | 1/2002 |
| WO | WO 2003/058646 | 7/2003 |
| WO | WO 2003/087737 | 10/2003 |
| WO | WO 2004/000111 | 12/2003 |
| WO | WO 2004/004411 | 1/2004 |
| WO | WO 2005/096931 | 10/2005 |
| WO | WO 2005/099562 | 10/2005 |
| WO | WO 2008/017246 | 2/2008 |
| WO | WO 2008/080469 | 7/2008 |
| WO | WO 2008/148172 | 12/2008 |
| WO | WO 2009/093159 | 7/2009 |
| WO | WO 2009/137524 | 11/2009 |

OTHER PUBLICATIONS

US 9,579,050 B2, 02/2017, Al-Ali (withdrawn)
Hsu, Schaum's Theory and Problems for Signals and Systems, McGraw-Hill, pp. 121, 1995.*
U.S. Appl. No. 14/133,173, Non-Invasive Monitoring of Respiratory Rate, Heart Rate and Apnea, filed Dec. 18, 2013.
U.S. Appl. No. 12/905,449, System for Determining Confidence in Respiratory Rate Measurements, filed Oct. 15, 2010.
U.S. Appl. No. 12/905,384, Respirator Processor, filed Oct. 15, 2010.
U.S. Appl. No. 12/905,489, Respiratory Pause Detector, filed Oct. 15, 2010.
U.S. Appl. No. 14/207,248, Acoustic Respiratory Event Processor, filed Mar. 12, 2014.
U.S. Appl. No. 13/076,423, Plethysmographic Respiration Processor, filed Mar. 30, 2011.
U.S. Appl. No. 13/651,283, Respiration Event Processor, filed Oct. 12, 2012.
U.S. Appl. No. 12/905,384, filed Oct. 10, 2010, Al-Ali et al.
U.S. Appl. No. 12/905,449, filed Oct. 15, 2010, Al-Ali et al.
U.S. Appl. No. 12/905,489, filed Oct. 15, 2010, Weber et al.
Analog Devices, 12-Bit Serial Input Multiplying D/A Converter, Product Data Sheet, 2000.
Chambrin, M-C.; "Alarms in the intensive care unit: how can the number of false alarms be reduced?"; Critical Care Aug. 2001, vol. 5 No. 4; p. 1-5.
Eldor et al., "A device for monitoring ventilation during anesthesia; the paratracheal audible respiratory monitor", Canadian Journal of Anesthesia, 1990, vol. 9, No. 1, p. 95-98.
Gorges, M. et al; "Improving Alarm Performance in the Medical Intensive Care Unit Using Delays and Clinical Context"; Technology, Computing, and Simulation; vol. 108, No. 5, May 2009; p. 1546-1552.
Imhoff, M. et al; "Alarm Algorithms in Critical Care Monitoring"; Anesth Analg 2006;102:1525-37.
International Search Report & Written Opinion, PCT Application PCT/US2010/052758, dated Feb. 10, 2011; 12 pages.
International Search Report & Written Opinion, PCT Application PCT/US2010/058981, dated Feb. 17, 2011; 11 pagfes.
International Search Report and Written Opinion issued in application No. PCT/US2010/052756 dated Feb. 6, 2012.
International Search Report, PCT Application PCT/CA2003/000536, dated Dec. 11, 2003; 2 pages.
International Search Report, PCT Application PCT/US2009/069287, dated Mar. 30, 2010; 7 pages.
Japanese Office Action for JP Application No. 2007-506626 dated Mar. 1, 2011.
Sierra et al., Monitoring Respiratory Rate Based on Tracheal Sounds. First Experiences, Proceedings of the 26th Annual Int'l Conf. of the IEEE EMBS (Sep. 2004), 317-320.
Watt, R. C.; "Alarms and Anesthesia. Challenges in the design of Intelligent systems for Patient Monitoring"; IEEE Engineering in Medicine and biology; Dec. 1993, p. 34-41.
Welch Allyn, ECG ASIC, Product Data Sheet, 2001.
Supplementary Partial European Search Report for International Application No. 05732095.4, dated Jun. 26, 2009 in 4 pages.
Theimer et al., "Definitions of audio features for music content description", Algorithm Engineering Report TR08-2-001, Feb. 2008.
Stewart, C., Larson, V., "Detection and classification of acoustic signals from fixed-wing aircraft," Systems Engineering, CH3051-0/91/0000-0025, IEEE, 1991.
Johnston, Development of a Signal Processing Library for Extraction of Sp02, HR, HRV, and RR from Photoplethysmographic Waveforms, Thesis: Degree of Master of Science, Worcester Polytechnic Institute, date of presentation/defense Jul. 17, 2006, date listed Jul. 27, 2006.

* cited by examiner

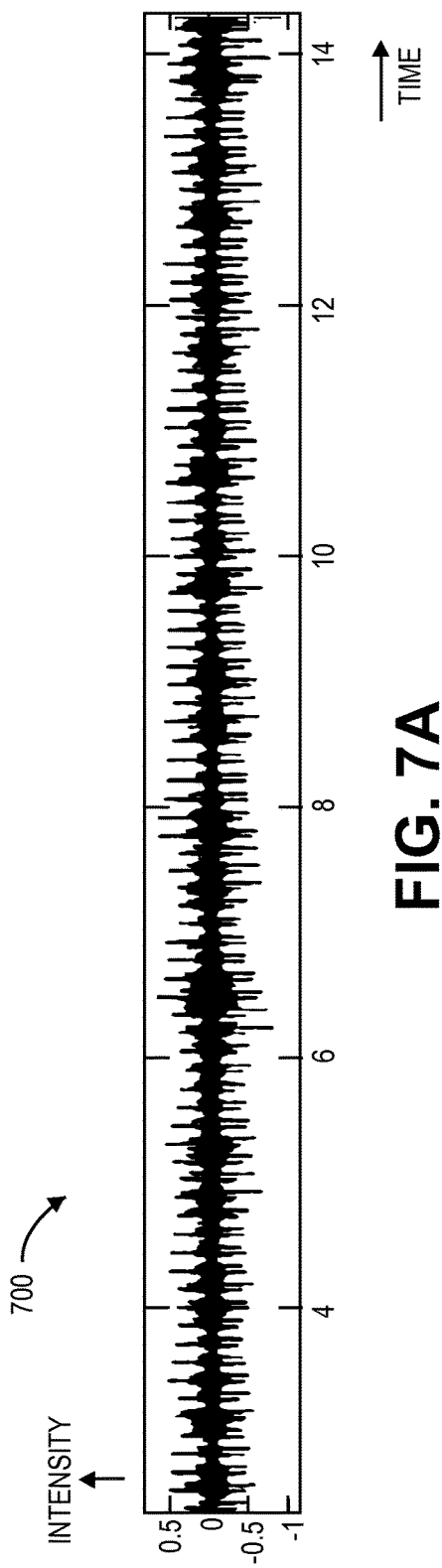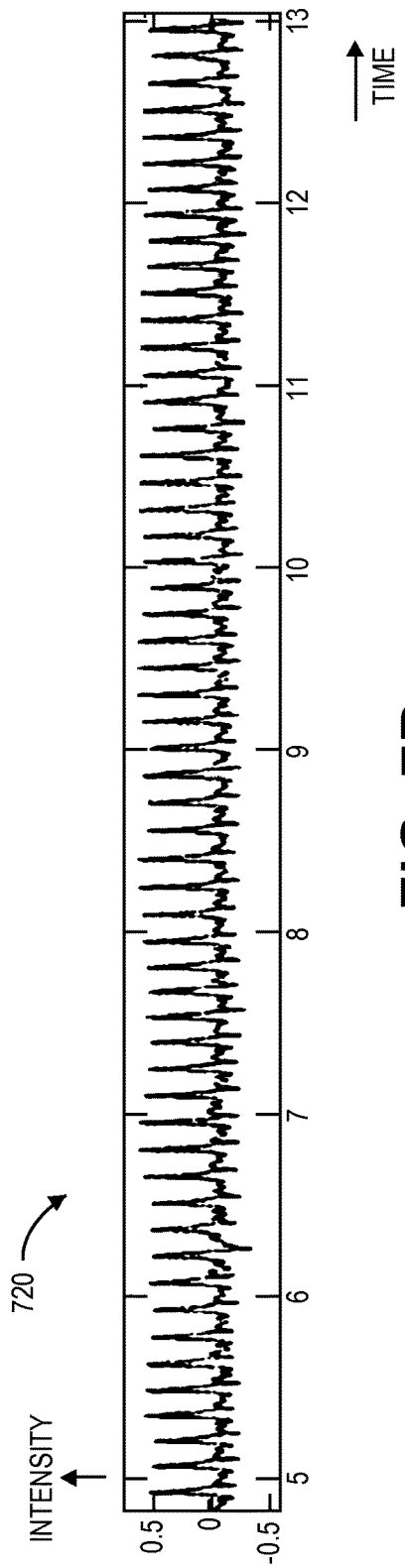

ACOUSTIC PULSE AND RESPIRATION MONITORING SYSTEM

REFERENCE TO RELATED APPLICATIONS

The present application is a continuation of U.S. patent application Ser. No. 14/206,900, filed Mar. 12, 2014, entitled "ACOUSTIC PULSE AND RESPIRATION MONITORING SYSTEM," which claims priority benefit from U.S. Provisional Application No. 61/780,412, filed Mar. 13, 2013, entitled "ACOUSTIC PULSE AND RESPIRATION MONITORING SYSTEM," the disclosures of which are incorporated herein by reference in their entirety.

BACKGROUND

The "piezoelectric effect" is the appearance of an electric potential and current across certain faces of a crystal when it is subjected to mechanical stresses. Due to their capacity to convert mechanical deformation into an electric voltage, piezoelectric crystals have been broadly used in devices such as transducers, strain gauges and microphones. However, before the crystals can be used in many of these applications they must be rendered into a form which suits the requirements of the application. In many applications, especially those involving the conversion of acoustic waves into a corresponding electric signal, piezoelectric membranes have been used.

Piezoelectric membranes are typically manufactured from polyvinylidene fluoride plastic film. The film is endowed with piezoelectric properties by stretching the plastic while it is placed under a high-poling voltage. By stretching the film, the film is polarized and the molecular structure of the plastic aligned. A thin layer of conductive metal (typically nickel-copper) is deposited on each side of the film to form electrode coatings to which connectors can be attached.

Piezoelectric membranes have a number of attributes that make them interesting for use in sound detection, including: a wide frequency range; a low acoustical impedance close to water and human tissue; a high dielectric strength; a good mechanical strength; and piezoelectric membranes are moisture resistant and inert to many chemicals.

SUMMARY

Acoustic sensors, such as piezoelectric membranes, can be used to determine respiration related parameters from an acoustic signal sensed from the neck of an individual, such as a medical patient. The determined respiration parameters can include parameters such as the individual's respiration rate in some implementations. As a result, the sensed acoustic signal can be filtered before signal processing to remove certain frequency components that may not be used to determine the respiration parameters. In one such embodiment, the sensed acoustic signal can be high-pass filtered to remove or diminish frequencies below about 100 Hz and pass frequencies above about 100 Hz because the determined respiration parameters may be determined based on frequency components of the sensed acoustic signal that may exceed about 100 Hz. However, such filtering can remove or diminish pulse information that may be included in the sensed acoustic signal.

The systems and methods of this disclosure, in some embodiments, advantageously may not high-pass filter a sensed acoustic signal to remove or diminish frequency components below about 100 Hz. Instead, the sensed acoustic signal can be high-pass filtered at a lower frequency, such as about 0.1 Hz, 1 Hz, 10 Hz, 30 Hz, 40 Hz, or the like. The filtered acoustic signal can be further filtered to remove or reduce effects on the acoustic signal of a sensing device, which is used to sense and/or process the acoustic signal, to thereby obtain a compensated signal that may correspond closely to a pulse signal of the individual. The compensated signal can then be used to determine numerous respiration and pulse parameters, such as the individual's respiration rate or pulse rate.

Acoustic sensors and associated processing modules that together form a sensing device can inherently filter and change signals output by the sensing device. For example, the mechanical properties of an acoustic sensor, such as the materials of the acoustic sensor or a match of the acoustic sensor to the skin of an individual, can influence an acoustic signal output by a sensing device. In addition, the electrical properties of a high-pass, band-pass, or low-pass filter module included in a sensing device can influence an acoustic signal output by the sensing device. Such filtering and changing of signals, unfortunately, can result in an acoustic signal output by a sensing device that may hide or mask an underlying physical signal detected by the sensing device. The output acoustic signal thus can be difficult to process for determining parameters for understanding the physiological condition of an individual.

The impact of a sensing device, including an acoustic sensor and one or more associated processing modules, on a detected acoustic signal can be understood in terms of a system transfer function. The sensing device can be considered to receive an input signal (for example, the vibration of an individual's skin) and then generate an output signal based on both the received input signal and a system transfer function. The sensing system, for instance, may be considered to output a signal that corresponds to the input signal after being influenced by the system transfer function.

Accordingly, the systems and methods of this disclosure, in some embodiments, can filter an acoustic signal so as to reverse or undo the effects on the acoustic signal of a sensing device used for sensing or processing the acoustic signal. An acoustic signal can be obtained as a result that corresponds closely to a physical signal detected by the sensing device. This acoustic signal desirably can be understood in terms of physical limitations, boundaries, or intuitions since the acoustic signal may correspond closely to a physical signal. For example, the acoustic signal can directly correspond to an expansion and contraction of the sensed skin of an individual, which can be useful in determining accurate and reliable respiration and pulse parameters for the individual.

One aspect of this disclosure provides a physiological monitoring system configured to determine one or more pulse or respiration parameters from one or more of an acoustic signal and a plethysmograph signal. Before determining respiration or pulse parameters from the acoustic signal, the acoustic signal can be integrated one or more times with respect to time. The physiological monitoring system can utilize the integrated acoustic signal to estimate a pulse rate based on pulses in the integrated acoustic signal and a respiration rate based on modulation of the integrated acoustic signal, among other parameters. The physiological monitoring system further can compare the determined parameters with predetermined values or pulse and respiration parameters determined based on a plethysmograph signal, for example, to activate alarms of the physiological monitor.

Advantageously, in certain embodiments, the pulse and respiration parameters determined in accordance with this disclosure can increase the robustness of a physiological monitoring system. For instance, the pulse and respiration parameters can provide one or more additional parameter values to validate the accuracy of parameters determined using one or more other physiological sensors. Moreover, the pulse and respiration parameters determined in accordance with this disclosure can be sensed closer to an individual's heart or chest than using one or more other types or placements of physiological sensors.

BRIEF DESCRIPTION OF THE DRAWINGS

FIG. 7A is an example acoustic signal processed by an acoustic signal processor;

FIG. 7B is an example filtered acoustic signal generated by a filter;

DETAILED DESCRIPTION

In various embodiments, a physiological monitoring system that includes an acoustic signal processing system can communicate with an acoustic sensor to measure or determine any of a variety of physiological parameters of a medical patient. For example, the physiological monitoring system can include an acoustic monitor. The acoustic monitor may, in an embodiment, be an acoustic respiratory monitor that can determine one or more respiratory parameters of the patient, including respiratory rate, expiratory flow, tidal volume, minute volume, apnea duration, breath sounds, rales, rhonchi, stridor, and changes in breath sounds such as decreased volume or change in airflow. In addition, in some implementations, the acoustic signal processing system can be used to monitor or determine other physiological sounds, such as patient heart rate to help with probe off detection, heart sounds (S1, S2, S3, S4, and murmurs), or change in heart sounds including normal to murmur or split heart sounds indicating fluid overload. Moreover, the acoustic signal processing system can further communicate with a second probe placed over the patient's chest for additional heart sound detection in some implementations.

In certain embodiments, the physiological monitoring system can include an electrocardiograph (ECG or EKG) that may measure or process electrical signals generated by the cardiac system of a patient. The ECG can include one or more sensors for measuring the electrical signals. In some implementations, the electrical signals can be obtained using the same sensors that may be used to obtain acoustic signals.

In certain embodiments, the physiological monitoring system can communicate with one or more additional sensors to determine other desired physiological parameters for a patient. For example, a photoplethysmograph sensor can be used to determine the concentrations of analytes contained in the patient's blood, such as oxyhemoglobin, carboxyhemoglobin, methemoglobin, other dyshemoglobins, total hemoglobin, fractional oxygen saturation, glucose, bilirubin, and/or other analytes. In another example, a capnograph can be used to determine the carbon dioxide content in inspired and expired air from a patient. In yet another example, one or more other sensors, such as a pneumotachometer for measuring air flow and a respiratory effort belt, can be used to determine blood pressure, flow rate, air flow, and fluid flow (first derivative of pressure). In certain embodiments, the sensors can be combined in a single processing system that can process the one or more signals output from the sensors on a single multi-function circuit board.

Figure 1A:
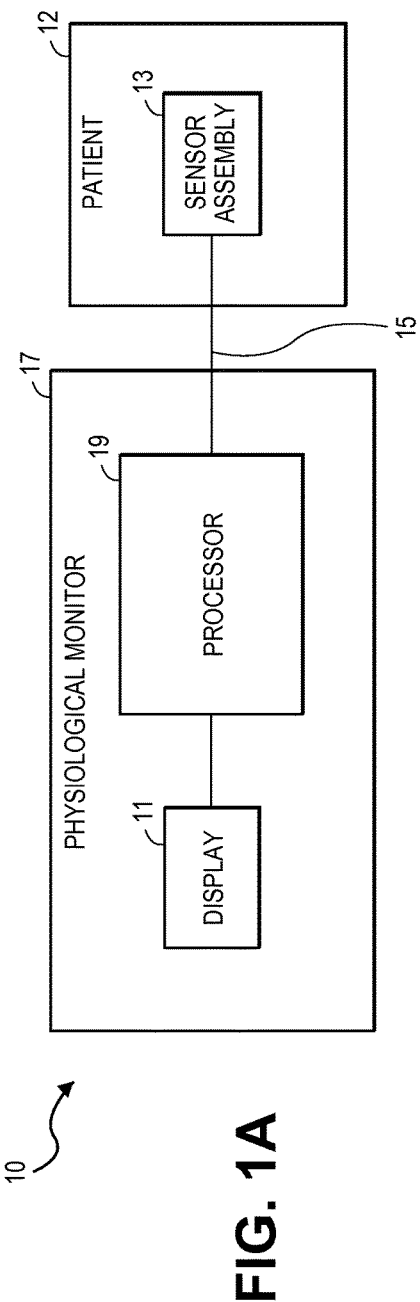
FIGS. 1A-B are block diagrams illustrating physiological monitoring systems.
Figure 1B:
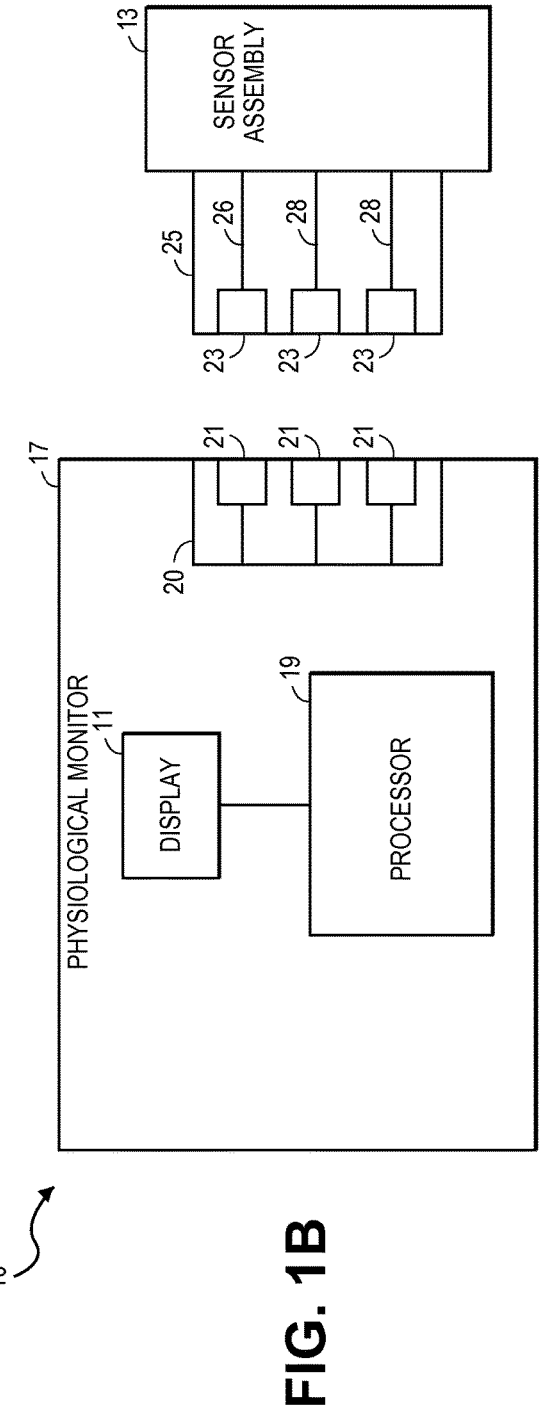
Figure 1C:
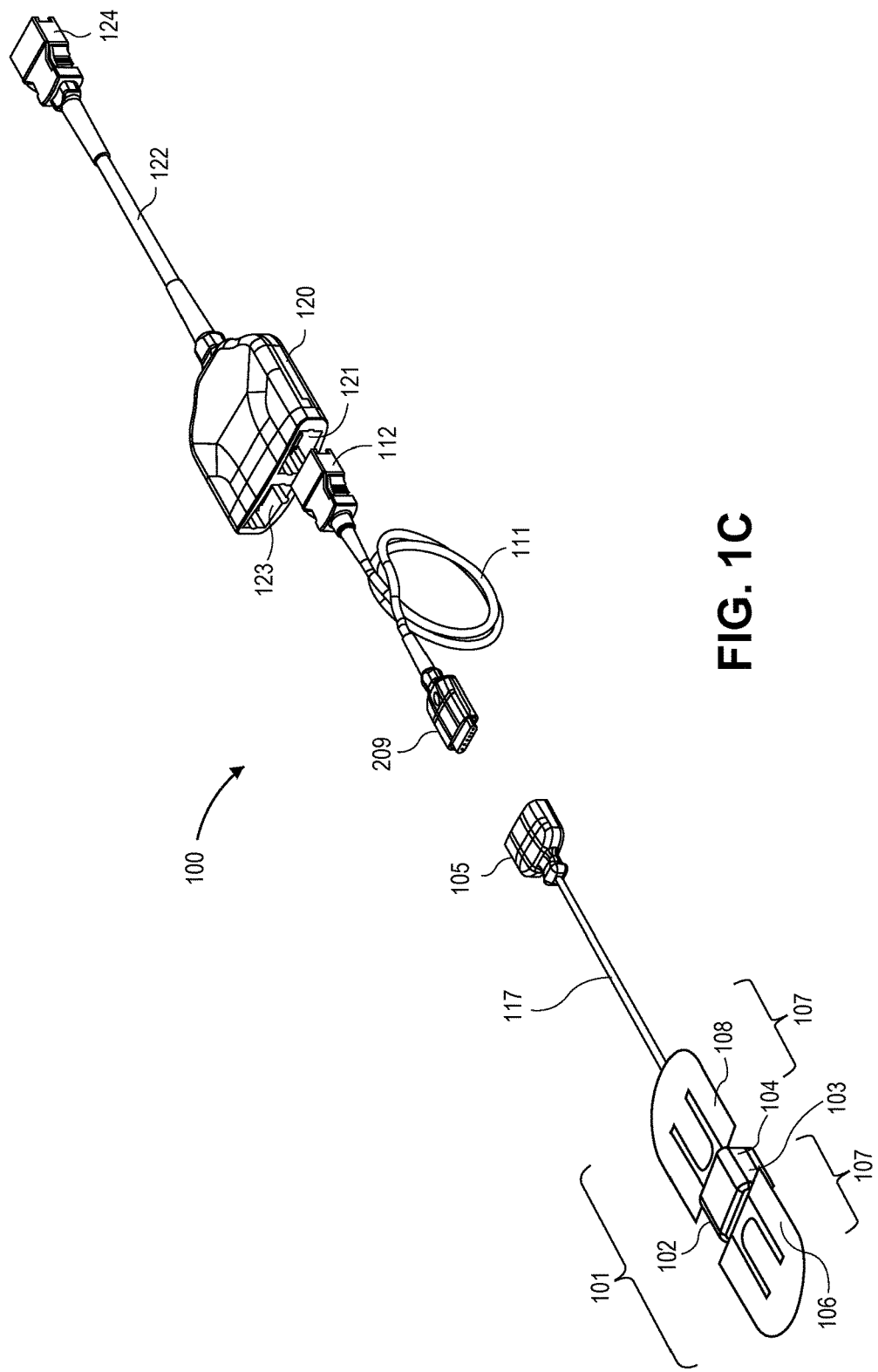
FIG. 1C is a top perspective view illustrating portions of a sensor system.

FIGS. 1A through 1C illustrate example patient monitoring systems, sensors, and cables that can be used to provide acoustic physiological monitoring, such as acoustic pulse and respiration monitoring, of a patient.

FIG. 1A shows an embodiment of a physiological monitoring system 10. In the monitoring system 10, a medical patient 12 can be monitored using one or more sensors 13, each of which can transmit a signal over a cable 15 or other communication link or medium to a physiological monitor 17. The physiological monitor 17 can include a processor 19 and, optionally, a display 11. The one or more sensors 13 can include sensing elements such as, for example, acoustic piezoelectric devices, electrical ECG leads, pulse oximetry sensors, or the like. The one or more sensors 13 can generate respective signals by sensing a physiological condition of the patient 12. The signals can then be processed by the processor 19. The processor 19 can communicate the processed signal to the display 11 if a display 11 is provided. In an embodiment, the display 11 is incorporated in the physiological monitor 17. In another embodiment, the display 11 is separate from the physiological monitor 17. The monitoring system 10 can, for instance, be a portable monitoring system or a pod, without a display, that may be adapted to provide physiological parameter data to a display.

For clarity, a single block is used to illustrate the one or more sensors 13 shown in FIG. 1A. It should be understood that the sensor 13 shown is intended to represent one or more sensors. In an embodiment, the one or more sensors 13 include a single sensor of one of the types described below. In another embodiment, the one or more sensors 13 include at least two acoustic sensors. In still another embodiment, the one or more sensors 13 include at least two acoustic sensors and one or more ECG sensors, pulse oximetry sensors, bioimpedance sensors, capnography sensors, or the like. Additional sensors of different types can also be included. Other combinations of numbers and types of sensors are also suitable for use with the physiological monitoring system 10.

In some embodiments of the system shown in FIG. 1A, the hardware used to receive and process signals from the sensors are housed within the same housing. In other embodiments, some of the hardware used to receive or process the signals can be housed within a separate housing. In addition, the physiological monitor 17 can include hardware, software, or both hardware and software, whether in one housing or multiple housings, usable to receive and process the signals transmitted by the one or more sensors 13.

As shown in FIG. 1B, the one or more sensors 13 can include a cable 25. The cable 25 can include three conductors within an electrical shielding. One conductor 26 can provide power to a physiological monitor 17, one conductor 28 can provide a ground signal to the physiological monitor 17, and one conductor 28 can transmit signals from the one or more sensors 13 to the physiological monitor 17. For multiple sensors implementations, one or more additional cables 115 can further be provided.

In some embodiments, the ground signal can be an earth ground, but in other embodiments, the ground signal may be a patient ground, sometimes referred to as a patient reference, a patient reference signal, a return, or a patient return. In some embodiments, the cable 25 can carry two conductors within an electrical shielding layer, and the shielding layer can act as the ground conductor. Electrical interfaces 23 in the cable 25 can enable the cable to electrically connect to electrical interfaces 21 in a connector 20 of the physiological monitor 17. In another embodiment, the sensor 13 and the physiological monitor 17 communicate wirelessly, such as via an IEEE standard (e.g., IEEE 802, IEEE 802.11 a/b/g/n, WiFi™, or Bluetooth™, etc.)

FIG. 1C illustrates an embodiment of a sensor system 100 including a sensor 101 suitable for use with the physiological monitors shown in FIGS. 1A and 1B. The sensor system 100 can include the sensor 101, a sensor cable 117, and a connector 105 attached to the sensor cable 117. The sensor 101 can include a shell 102, an acoustic coupler, 103 and a frame 104, which may also be referred to as a sensor support, configured to house certain componentry of the sensor 101, and an attachment portion 107 positioned on the sensor 101 and configured to attach the sensor 101 to the patient.

The sensor 101 can be removably attached to an instrument cable 111 via an instrument cable connector 109. The instrument cable 111 can be attached to a cable hub 120, which can include a port 121 for receiving a connector 112 of the instrument cable 111 and a second port 123 for receiving another cable. In certain embodiments, the second port 123 can receive a cable connected to a pulse oximetry or other sensor. In addition, the cable hub 120 could include additional ports for receiving one or more additional cables in other embodiments. The hub includes a cable 122 which terminates in a connector 124 adapted to connect to a physiological monitor. In another embodiment, no hub may be provided and the acoustic sensor 101 can be connected directly to the monitor, via an instrument cable 111, or directly by the sensor cable 117, for example. Examples of compatible hubs are described in U.S. patent application Ser. No. 12/904,775, filed on Oct. 14, 2010, which is incorporated by reference in its entirety herein. Examples of acoustic sensors are described in U.S. patent application Ser. No. 14/030,268, filed on Sep. 18, 2013, which is incorporated by reference in its entirety herein.

The component or group of components between the sensor 101 and monitor can be referred to generally as a cabling apparatus. For example, where one or more of the following components are included, such components or combinations thereof can be referred to as a cabling apparatus: the sensor cable 117, the connector 105, the cable connector 109, the instrument cable 111, the hub 120, the cable 122, or the connector 124. It should be noted that one or more of these components may not be included, and that one or more other components may be included between the sensor 101 and the monitor to form the cabling apparatus.

In an embodiment, the acoustic sensor 101 includes one or more sensing elements, such as, for example, one or more piezoelectric devices or other acoustic sensing devices. Where a piezoelectric membrane may be used, a thin layer of conductive metal can be deposited on each side of the film as electrode coatings, forming electrical poles. The opposing surfaces or poles may be referred to as an anode and cathode, respectively. Each sensing element can be configured to mechanically deform in response to sounds emanating from the patient and generate a corresponding voltage potential across the electrical poles of the sensing element.

The shell 102 can house a frame or other support structure configured to support various components of the sensor 101. The one or more sensing elements can be generally wrapped in tension around the frame. For example, the sensing elements can be positioned across an acoustic cavity disposed on the bottom surface of the frame. Thus, the sensing elements can be free to respond to acoustic waves incident upon them, resulting in corresponding induced voltages across the poles of the sensing elements.

Additionally, the shell 102 can include an acoustic coupler, which advantageously can improve the coupling between the source (for example, the patient's body) of the signal to be measured by the sensor and the sensing element. The acoustic coupler can include a bump positioned to apply pressure to the sensing element so as to bias the sensing element in tension. In one example, the bump can be positioned against the portion of the sensing element that may be stretched across the cavity of the frame. The acoustic coupler further can include a protrusion on the upper portion of the inner lining, which exerts pressure on the backbone 110 and other internal components of the sensor 101.

The attachment portion 107 can help secure the sensor assembly 101 to the patient. The illustrated attachment portion 107 can include first and second attachment arms 106, 108. The attachment arms can be made of any number of materials, such as plastic, metal or fiber. Furthermore, the attachment arms can be integrated with the backbone. The underside of the attachment arms 106, 108 include patient adhesive (for example, tape, glue, a suction device, or the like), which can be used to secure the sensor 101 to a patient's skin. The attachment portion 107 further can include a resilient backbone member 110 which may extend into and form a portion of the attachment arms 106, 108. The backbone 110 can be placed above or below the attachment arms 106, 108, or can be placed between an upper portion and a lower portion of the attachment arms 106, 108. Furthermore, the backbone can be constructed of any number of resilient materials, such as plastic, metal, fiber, combinations thereof, or the like.

As the attachment arms 106, 108 may be brought down into contact with the patient's skin on either side of the sensor 102, the adhesive affixes to the patient. Moreover, the resiliency of the backbone 110 can cause the sensor 101 to be beneficially biased in tension against the patient's skin or reduces stress on the connection between the patient adhesive and the skin. Further examples of compatible attachment portions, associated functionality and advantages are described in U.S. application Ser. No. 12/643,939 (the '939 application), which is incorporated by reference herein. For example, embodiments of attachment portions are shown in and described with respect to FIGS. 2B, 2C, 9A-9D and 10 of the '939 application, which is explicitly incorporated by reference herein in its entirety.

The acoustic sensor 101 can further include circuitry for detecting and transmitting information related to biological sounds to the physiological monitor. These biological sounds can include heart, breathing, or digestive system sounds, in addition to many other physiological phenomena. The acoustic sensor 101 in certain embodiments is a biological sound sensor, such as the sensors described herein. In some embodiments, the biological sound sensor is one of the sensors such as those described in U.S. patent application Ser. No. 12/044,883, filed Mar. 7, 2008, which is incorporated in its entirety by reference herein. In other embodiments, the acoustic sensor 101 can be a biological sound sensor such as those described in the '939 application. Other embodiments can include other suitable acoustic sensors. For example, in certain embodiments, compatible acoustic sensors can be configured to provide a variety of auscultation functions, including live or recorded audio output (e.g., continuous audio output) for listening to patient bodily or speech sounds. Examples of such sensors and sensors capable of providing other compatible functionality can be found in U.S. patent application Ser. No. 12/905,036, filed on Oct. 14, 2010, which is incorporated by reference herein in its entirety.

While the sensor system 100 has been provided as one example sensor system, embodiments described herein are compatible with a variety of sensors and associated components.

Figure 2A:
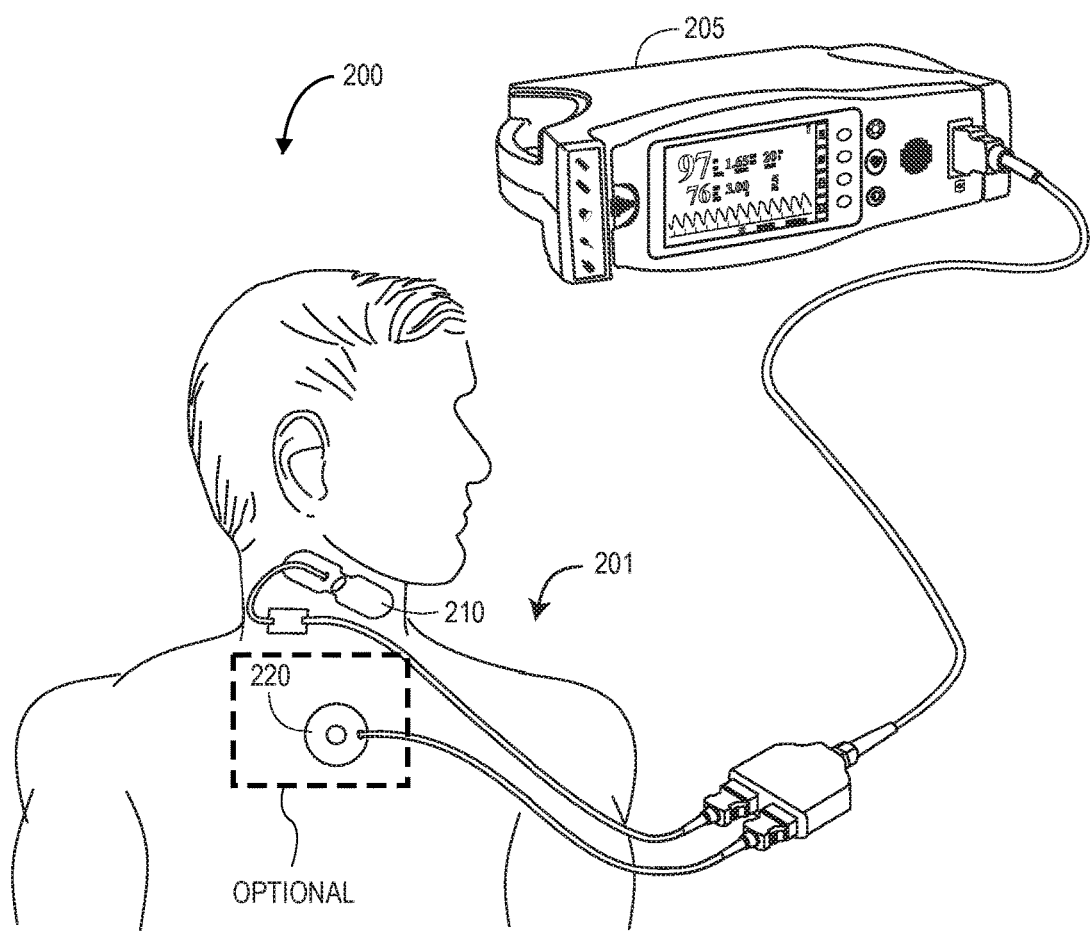
FIG. 2A illustrates an acoustic neck sensor and a chest sensor for physiological measurements.
Figure 2B:
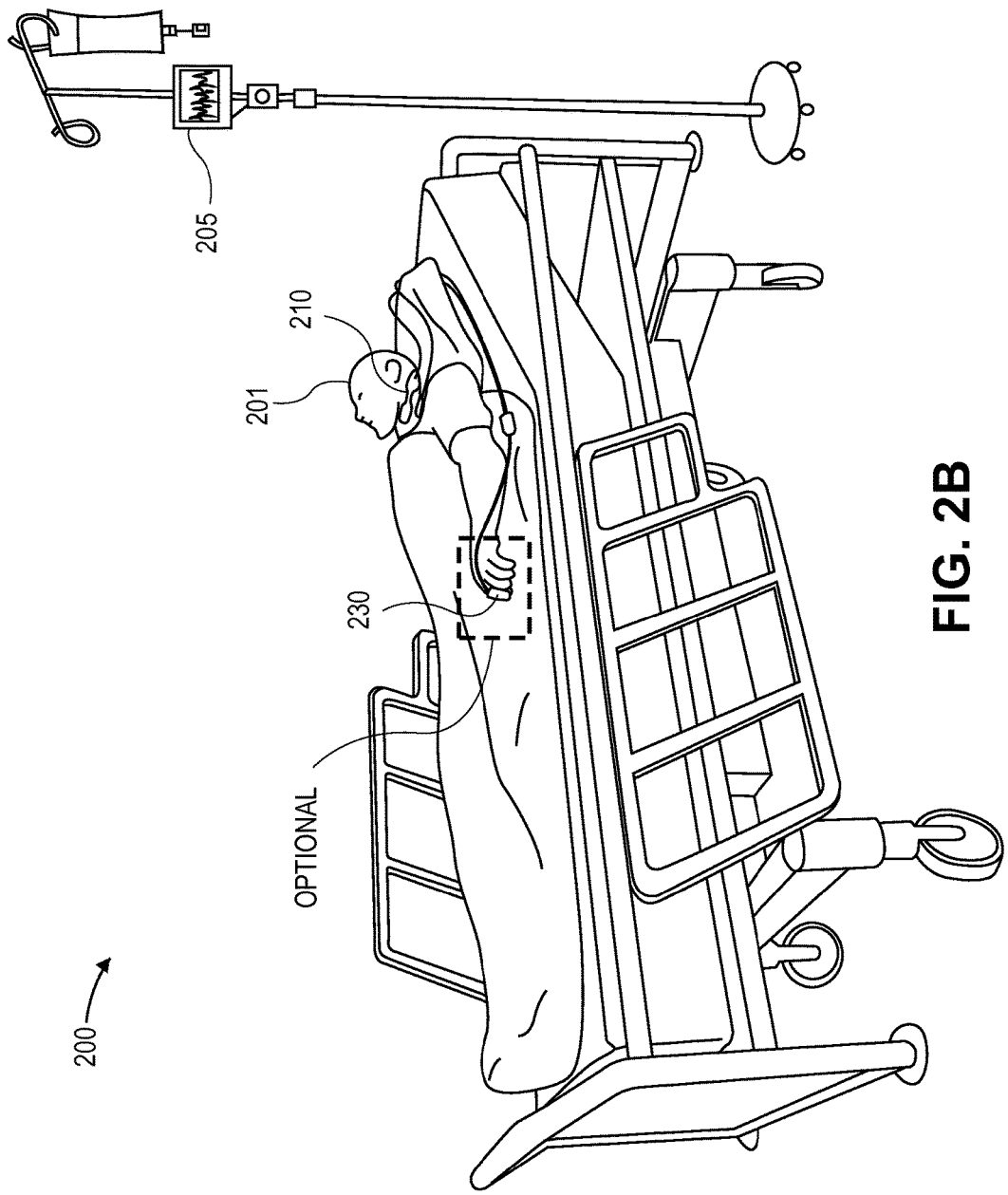
FIG. 2B illustrates an acoustic neck sensor and a plethysmograph for physiological measurements.

FIGS. 2A-B illustrate physiological acoustic monitoring system 200 embodiments having sensors in communication with a physiological monitor 205. As shown in FIG. 2A, a first acoustic sensor 210 can be neck-mounted and utilized for monitoring body sounds and deriving one or more physiological parameters, such as the pulse or respiration rate of the patient 201. An optional second acoustic sensor 220 can be utilized to monitor body sounds. In an embodiment, the body sound sensor 220 may be chest-mounted for monaural heart sound monitoring and for determination of heart rate. In another embodiment, the second acoustic sensor 220 can include an additional body sound sensor mounted proximate the same body site, but with sufficient spatial separation to allow for stereo sensor reception. As shown in FIG. 2B, an optional plethysmograph sensor 230 coupled to the finger of a patient can further be utilized for monitoring and deriving one or more physiological parameters, such as respiration or pulse rate of the patent 201.

Figure 3:
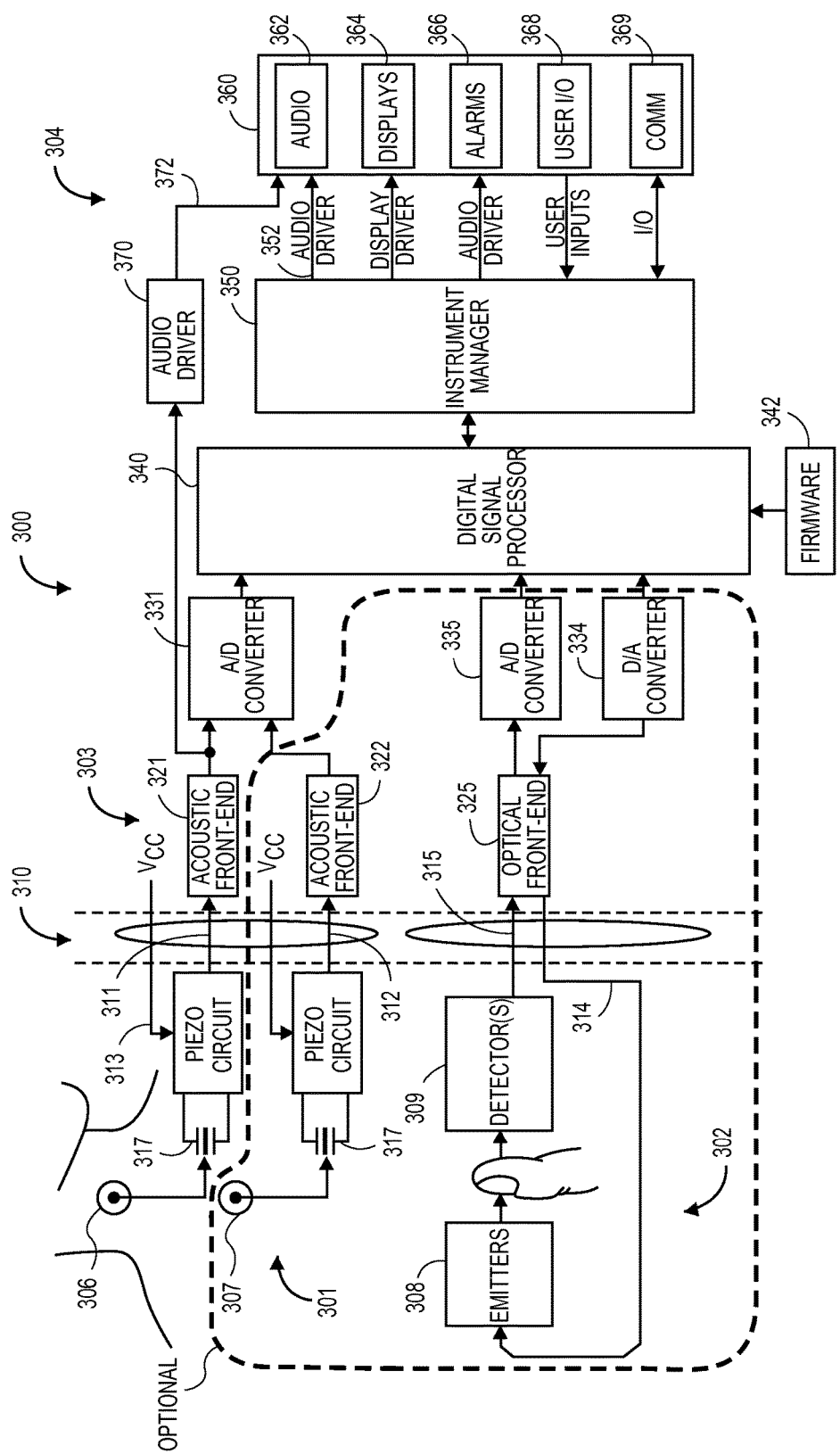
FIG. 3 is a schematic diagram of acoustic and optical sensors and sensor drive elements and a corresponding digital signal processor and I/O drive elements.

FIG. 3 illustrates acoustic 301 and optical 302 sensors and sensor drive elements 303 and a corresponding digital signal processor 340 and I/O drive elements 304. Some elements in FIG. 3, such as piezoelectric membrane 317 and optical front-end 325, are denoted as within a dashed area as optional features and can be included individually or as sets of elements in some embodiments of physiological monitoring system.

A multi-acoustic sensor configuration 301 can include a power interface 313, piezo circuits and a piezoelectric membrane 317 corresponding to each sensor head 306, 307. The piezoelectric membrane 317 can sense vibrations and generate a voltage in response to the vibrations. The signal generated by the piezoelectric membrane can be communicated to the piezo circuit and transmitted to the monitor 205 (FIGS. 2A-B) for signal conditioning and processing. The piezo circuit can decouple the power supply 313 and perform preliminary signal conditioning. In an embodiment, the piezo circuit 316 can include clamping diodes to provide electrostatic discharge (ESD) protection and a mid-level voltage DC offset for the piezoelectric signal to ride on, to be superimposed on, or to be added to. The piezo circuit may also, for instance, have a high pass filter to eliminate unwanted low frequencies, such as below about 100 Hz for some breath sound applications or below about 30 Hz for some pulse sound applications, and an op amp to provide gain to the piezoelectric signal. The piezo circuit may also have a low pass filter on the output of the op amp to filter out unwanted high frequencies. In an embodiment, a high pass filter can be provided on the output in addition to or instead of the low pass filter. The piezo circuit may also provide impedance compensation to the piezoelectric membrane, such as a series/parallel combination used to control the signal level strength and frequency of interest that can be input to the op amp. In one embodiment, the impedance compensation can be used to minimize the variation of the piezoelectric element output. The impedance compensation can be constructed of any combination of resistive, capacitive, and inductive elements, such as RC or RLC circuits.

As shown in FIG. 3, a physiological acoustic monitor 300 embodiment can drive and process signals from the multi-acoustic sensor 301 and the optical sensor 302. The monitor 300 can include one or more acoustic front-ends 321, 322, an analog-to-digital (A/D) converter 331, an audio driver 370 and a digital signal processor (DSP) 340. The DSP 340 can include a wide variety of data or signal processors capable of executing programs for determining physiological parameters from input data. An optical front-end 325, digital-to-analog (D/A) converters 334 and an A/D converter 335 can drive emitters 308 and transform resulting composite analog intensity signal(s) from light sensitive detector(s) 309 received via a sensor cable 310 into digital data input to the DSP 340. The acoustic front-ends 321, 322 and A/D converter 331 can transform analog acoustic signals from piezoelectric elements 301 into digital data input to the DSP 340. The A/D converter 331 is shown as having a two-channel analog input and a multiplexed digital output to the DSP. In another embodiment, each front-end, can communicate with a dedicated single channel A/D converter generating two independent digital outputs to the DSP. An acoustic front-end 321 can also feed an acoustic sensor signal 311 directly into an audio driver 370 for direct and continuous acoustic reproduction of an unprocessed (raw) sensor signal by a speaker, earphones or other audio transducer 362.

Also shown in FIG. 3, the monitor 300 may also have an instrument manager 350 that communicates between the DSP 340 and input/output 360. One or more I/O devices 360 can communicate with the instrument manager 350 including displays, alarms, user I/O and instrument communication ports. Alarms 366 may be audible or visual indicators or both. The user I/O 368 may be, as examples, keypads, touch screens, pointing devices or voice recognition devices, or the like. The displays 364 can be indicators, numeric, or graphics for displaying one or more of various physiological parameters or acoustic data. The instrument manager 350 may also be capable of storing or displaying historical or trending data related to one or more of parameters or acoustic data.

Further shown in FIG. 3, the physiological acoustic monitor 300 may also have a "push-to-talk" feature that provides a "listen on demand" capability. For example, a button 368 on the monitor can be pushed or otherwise actuated so as to initiate acoustic sounds to be sent to a speaker, handheld device, or other listening device, either directly or via a network. The monitor 300 may also have a "mode selector" button or switch 368 that can determine the acoustic content provided to a listener, either local or remote. These controls may be actuated local or at a distance by a remote listener. In an embodiment, push on demand audio occurs on an alarm condition in lieu of or in addition to an audio alarm. Controls 368 may include output filters like on a high quality stereo system so that a clinician or other user could selectively emphasize or deemphasize certain frequencies so as to hone-in on particular body sounds or characteristics.

In various embodiments, the monitor 300 can include one or more processor boards installed within and used for communicating with a host instrument. Generally, a processor board incorporates the front-end, drivers, converters and DSP. Accordingly, the processor board can derive physiological parameters and communicate values for those parameters to the host instrument. Correspondingly, the host instrument can incorporate the instrument manager and I/O devices. The processor board may also include one or more microcontrollers for board management, including, for example, communications of calculated parameter data or the like to the host instrument.

Communications 369 may transmit or receive acoustic data or audio waveforms via local area or wide area data networks or cellular networks. Controls may cause the audio processor to amplify, filter, shape or otherwise process audio waveforms so as to emphasize, isolate, deemphasize or otherwise modify various features of the audio waveform or spectrum. In addition, switches, such as a "push to play" button can initiate audio output of live or recorded acoustic data. Controls may also initiate or direct communications.

Figure 4:
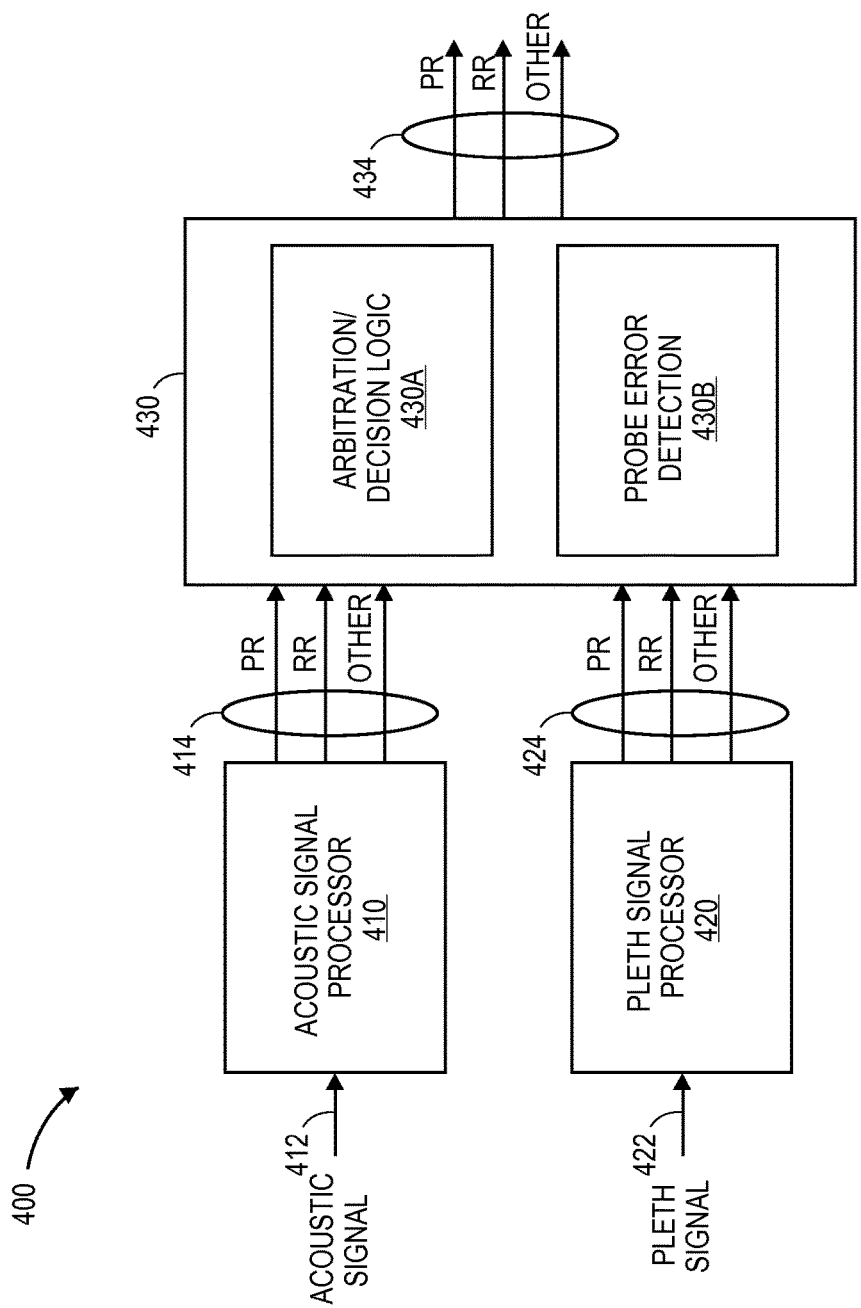
FIG. 4 is a block diagram of a pulse and respiration processor of a physiological monitor that includes an acoustic signal processor and a plethysmograph signal processor.

FIG. 4 is a block diagram of a pulse and respiration processor 400 of a physiological monitor that can include an acoustic signal processor 410, a plethysmograph ("pleth") signal processor 420, and a collection processing module 430. The acoustic signal processor 410 can include, for instance, any of the acoustic signal processors described in this disclosure. The plethysmograph signal processor 420 includes, for instance, any of the plethysmograph signal processors described in this disclosure. The one or more processors 19 of FIGS. 1A-B and DSP 340 of FIG. 3 can include the pulse and respiration processor 400.

The pulse and respiration processor 400 can determine one or more pulse or respiration parameters from one or more of an acoustic signal 412 and a plethysmograph signal 422. The acoustic signal processor 410 can receive an input acoustic signal 412, such as an acoustic signal obtained from the neck of an individual via the first acoustic sensor 210 of FIGS. 2A-B or the sensor head 306 of FIG. 3. The acoustic signal 412 can correspond to a signal received from the A/D converter 331 of FIG. 3. The plethysmograph signal processor 420 can receive the input plethysmograph signal 422, such as a plethysomographic signal obtained from the finger of a patient via plethysmograph sensor 230 of FIG. 2B or optical sensor 302 of FIG. 3. The plethysomographic signal can correspond to a signal received from the A/D converter 335 of FIG. 3.

The acoustic signal processor 410 and plethysmograph signal processor 420 can each respectively determine pulse and respiration parameters, such as a pulse rate ("PR") and respiration rate ("RR") of a patient. The acoustic signal processor 410 can output 414 the parameters determined based on the acoustic signal 412 to the collection processing module 430, and plethysmograph signal processor 420 can output 424 the parameters determined based on the plethysmograph signal 422 to the collection processing module 430. The collection processing module 430 can include a decision logic module 430A (sometimes referred to as an arbiter or arbitration module) and a probe error detection module 430B. The collection processing module 430 can perform processing of received parameters and output 434 arbitrated parameters for additional processing or detected probe errors, such as for triggering alarm conditions corresponding to the status of a patient.

In some embodiments, the pulse and respiration processor 400 can determine other pulse or respiration information, such as estimating a carotid intensity or respiration events. Such carotid intensity information may be used as an indication of blood pressure changes or pulse variability of an individual. The respiratory events can include information regarding a time when inspiration or expiration begin (Ti or Te, respectively), a time duration of an inspiration or an expiration (Tie or Tei, respectively), a ratio of the time duration of inspiration to expiration, or of expiration to inspiration (Tie/Tei or Tei/Tie, respectively), or some other respiratory event (e.g., conclusion of inspiration or expiration, midpoint of inspiration or expiration, or any other marker indicating a specific time within the respiratory cycle, or the like). Such respiratory event information may be used to further identify the occurrence of various respiratory conditions, such as apnea, occlusion of the breathing passageway, or snoring, for example.

Figure 5:
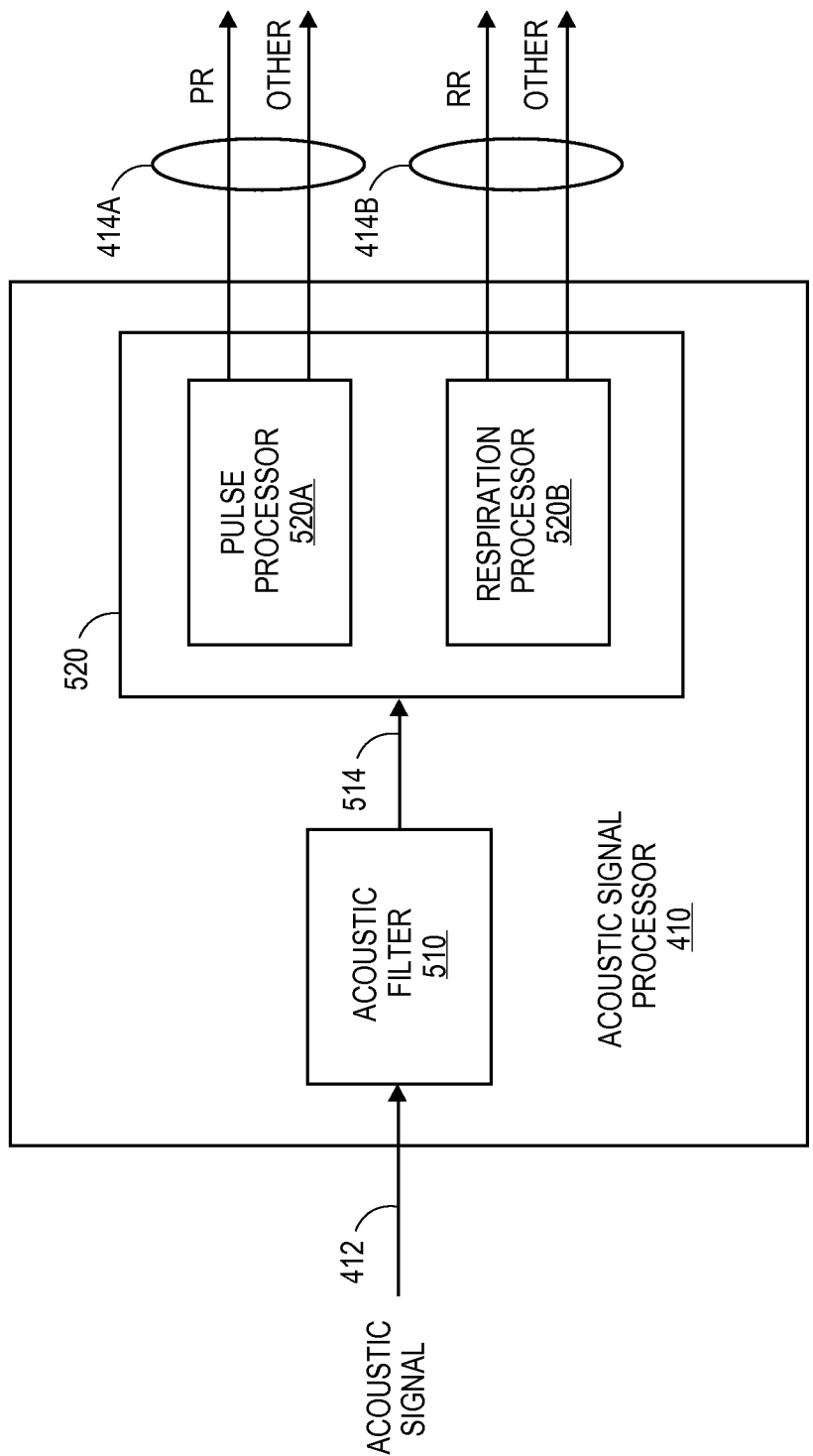
FIG. 5 is a block diagram of an example acoustic signal processor.

FIG. 5 is a block diagram of the acoustic signal processor 410 according to one embodiment. As illustrated, the acoustic signal processor 410 can include an acoustic filter 510 and an acoustic signal processing module 520. The acoustic filter 510 can filter the acoustic signal 412 to perform an inverse filtering relative to a transfer function of a sensing device (for example, including the piezoelectric membrane 317 and associated processing circuitry) used to sense the acoustic signal from the patient. The acoustic filter 510 can, for instance, perform a deconvolution using the transfer function of the sensing device and the acoustic signal 412 to undo, reverse, or diminish the impact of the sensing device on the acoustic signal 412. In one implementation, where the transfer function for a sensing device results in one or more derivatives with respect to time being performed on the detected acoustic signal, the acoustic filter 510 can integrate the acoustic signal 412 one or more times with respect to time to obtain a filtered acoustic signal 514 corresponding to the carotid pulse of an individual. A sensing device can have a transfer function that results in one or more derivatives with respect to time being performed on the detected acoustic signal when, for example, the sensing device may include one or more high-pass filters. Each high-pass filter in a sensing device can function as a differentiator of the acoustic signal. For instance, a sensing device may include a piezoelectric membrane, which can function as a high-pass filter of an acoustic signal, as well as one or more cutoff high-pass filters.

In some embodiments, the transfer function for a particular sensing device can be programmed or determined for the acoustic filter 510 at manufacture, setup-time, or runtime of a physiological monitor. In one example, a known input signal, which has an expected output signal, can be provided to the sensing device at manufacture. By analyzing the actual output signal, expected output signal, and known input signal, the transfer function for the particular sensing device can be determined and then stored to a memory of the monitor for later retrieval. In another example, the outputs of different sensors that may be connected to the same input signal can be compared at setup-time and used to determine the transfer function. Again, the determined transfer function can be stored to a memory of the monitor for later retrieval. In other implementations, one or more other approaches additionally or alternatively can be used to determine the transfer function for a particular sensing device.

The acoustic signal processing module 520 can include a pulse processor 520A and respiration processor 520B configured to determine one or more pulse or respiration parameters, respectively, based on the filtered acoustic signal 514. The pulse processor 520A and respiration processor 520B can output the determined pulse and respiration parameters 414A, 414B for further processing, such as by the collection processing module 430 of FIG. 4. In some embodiments, the respiration processor 520B can process the filtered signal acoustic signal 514 to determine one or more respiration parameters, such as respiratory rate, as disclosed in U.S. patent application Ser. No. 14/201,566, filed on Mar. 7, 2014, which is incorporated herein by reference in its entirety.

Figure 6:
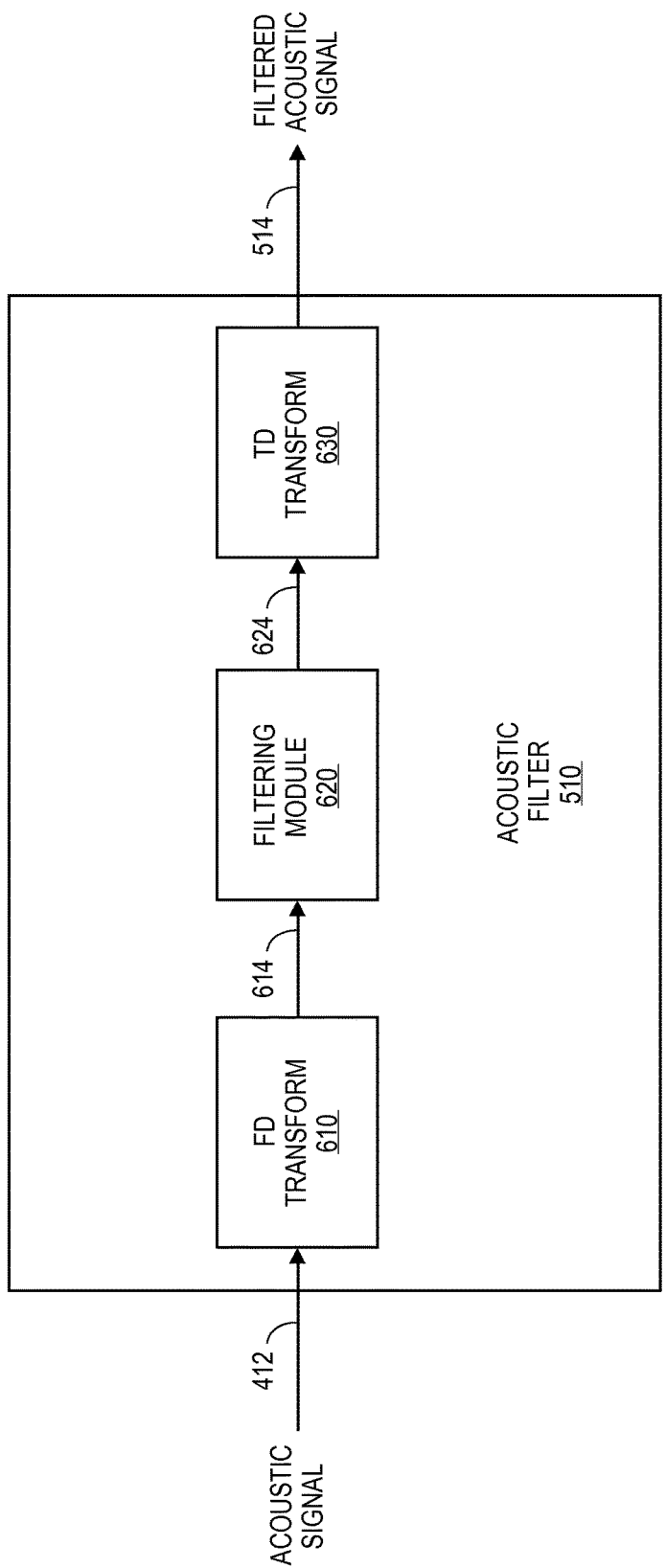
FIG. 6 is a block diagram of an example acoustic filter.

FIG. 6 is a block diagram of the acoustic filter 510 according to one embodiment. The acoustic filter 510 can filter the acoustic signal 412 in the frequency domain to reverse the effects of a transfer function of a sensing device used to sense the acoustic signal from the patient. The acoustic filter 510 can, in one implementation, integrate the acoustic signal 412 one or more times with respect to time to generate the filtered acoustic signal 514. In some embodiments, the acoustic filter 510 can integrate the acoustic signal 412 twice with respect to time to obtain the filtered acoustic signal 514. The filtered acoustic signal 514 can advantageously be a signal corresponding to an individual's carotid pulse and has relatively minimal noise or few other dominating frequency components. The filtered acoustic signal 514 can enable the straightforward determination of numerous characteristics indicative of pulse or respiration parameters of an individual.

As illustrated in FIG. 6, the acoustic filter 510 can include a frequency domain ("FD") transform module 610, a filtering module 620, and a time domain ("TD") transform module 630. The FD transform module 610 and TD transform module 630 together can enable performance of filtering by the filtering module 620 in a domain other than the time domain. Advantageously, in certain embodiments, performing filtering, such as integration, in the frequency domain can reduce the complexity of calculations when performing filtering. For instance, integrating in the frequency domain can permit integration calculations without accounting for additional constants that may be added if the integration may be performed in the time domain.

The frequency domain transform module 610 can receive the input acoustic signal 412 and transform the acoustic signal 412 to generate a frequency domain equivalent transformed signal 614. In one embodiment, the frequency domain transform module 610 can perform a fast Fourier transform ("FFT") of the acoustic signal 412 to generate the transformed signal 614. The filtering module 620 can receive the transformed signal 614 and, in the case of integration filtering, scale the transformed signal 614 by a frequency function, such as a function proportional to $(2\pi f)^{-2}$, to generate a scaled signal 624. The filtering module 620 can thus integrate the transformed signal 614 with respect to time in the frequency domain. The time domain transform module 630 can then transform the scaled signal 624 to a time domain equivalent filtered acoustic signal 514. In one embodiment, the time domain transform module 630 can perform an inverse fast Fourier transform ("IFFT") of the scaled signal 624 to generate the filtered acoustic signal 514.

FIG. 7A is a normalized acoustic signal 700, such as the acoustic signal 412 of FIGS. 4-6, processed by an acoustic signal processor, such as the acoustic signal processor 410 of FIGS. 4 and 5. The acoustic signal 700 can be sensed from the neck of a patient via an acoustic sensor, such as the first acoustic sensor 210 of FIGS. 2A-B or the sensor head 306 of FIG. 3. The acoustic signal 700 is shown plotted on an intensity axis versus a time axis. As can be seen in FIG. 7A, the acoustic signal 700 can be a relatively chaotic signal, including numerous frequency components ranging from low to high frequency components.

In one implementation, the steps of sensing and processing the acoustic signal 700 from an individual's neck can result in a differentiation with respect to time of the individual's physiological pulse signal. Accordingly, the acoustic signal 700 can be integrated with respect to time to reverse one or more differentiations during sensing and processing. For example, the piezo circuits illustrated in FIG. 3 can output a signal corresponding to the derivative of the sensed motion of the skin of a patient. Further, before processing the signal at the DSP, a high-pass filter can be utilized and thus output the derivative with respect to time of the received signals from the piezo circuits. As a result, advantageously, in certain embodiments, the acoustic signal 700 can be filtered by an acoustic filter, such as acoustic filter 510 of FIGS. 5 and 6, by computing the double integral of the acoustic signal to obtain a signal corresponding to an individual's carotid pulse that may have relatively minimal noise or few other dominating frequency components.

FIG. 7B is a normalized filtered acoustic signal 720 generated by a filter, such as the acoustic filter 510 of FIGS. 5 and 6. The acoustic signal 700 of FIG. 7A may have been integrated twice with respect to time to generate the filtered acoustic signal 720. The filtered acoustic signal 720 is shown plotted on an intensity axis versus a time axis. As can be seen in FIG. 7B, the filtered acoustic signal 720 can be a relatively ordered signal, including fewer frequency components than the acoustic signal 700 of FIG. 7A.

Figure 7C:
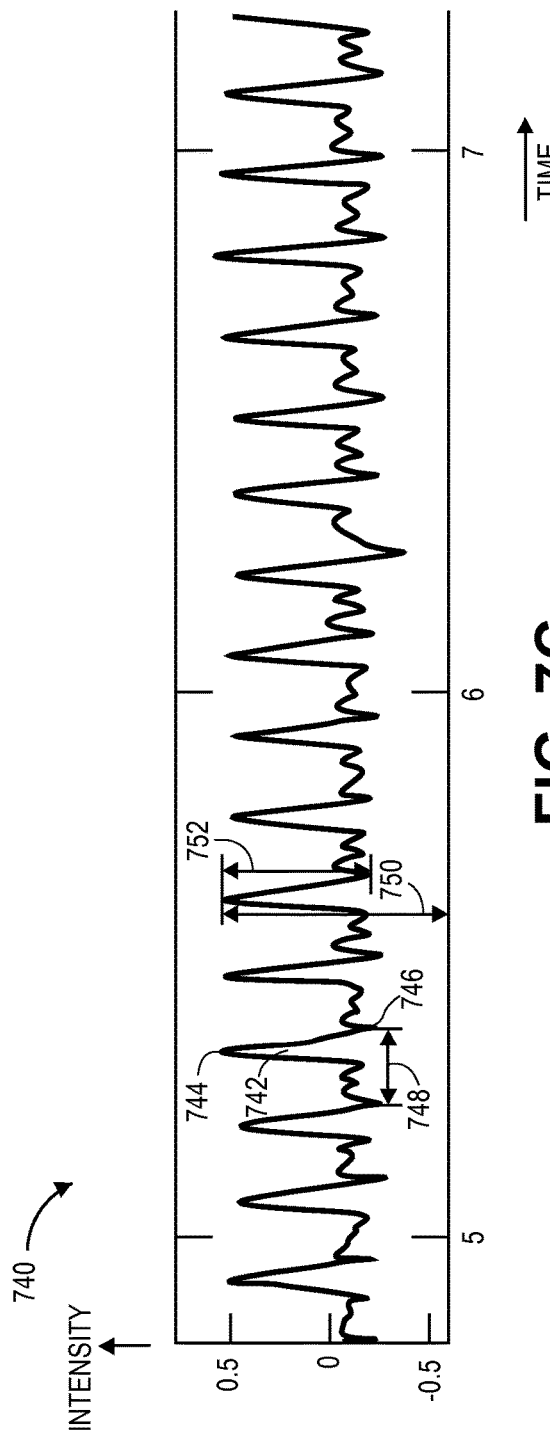
FIG. 7C is another example filtered acoustic signal generated by a filter.

FIG. 7C is another normalized filtered acoustic signal 740 generated by a filter, such as the acoustic filter of FIGS. 5 and 6. The filtered acoustic signal 740 can be a closer view of the filtered acoustic signal 720 of FIG. 7B. The filtered acoustic signal 740 is shown plotted on an intensity axis versus a time axis. Advantageously, in certain embodiments, the filtered acoustic signal 740 can be used by the acoustic signal processing module 520 of FIG. 5 to determine numerous pulse and respiration parameters of an individual.

The filtered acoustic signal 740 can have multiple pulses 742, each with a peak 744 and a valley 746 and extending over a time period 748, where the reciprocal of the time period 748 may equal a pulse rate. A carotid index (CI) value can be defined for each pulse 742:

$$CI = AC/DC \qquad (1)$$

where "AC" 752 designates a peak amplitude 744 minus a valley amplitude 746 for a particular pulse, "DC" 750 designates a peak amplitude 744 relative to a particular intensity level. A pulse variability measure can be calculated that may be responsive to the magnitude of pulse variations, such as the amplitude modulation described with respect to FIG. 7D and depicted by envelope 770 of FIG. 7D, for example. One pulse variability measure can be a pulse variability index (PVI). In an embodiment, PVI is calculated as:

$$PVI = CI_{MAX} - CI_{MIN}/CI_{MAX} \times 100 \qquad (2)$$

where "$CI_{MAX}$" designates a maximum CI over a particular period of time and "$CI_{MIN}$" designates a minimum CI over the particular period of time. Thus, PVI can be the CI variation, expressed as a percentage of the maximum CI. Advantageously, in certain embodiments, pulse variability measures such as PVI can provide a parameter indicative of an individual's physical condition or health.

The pulse processor 520A of the acoustic signal processing module 520 can analyze the filtered acoustic signal 740 as discussed with respect to FIG. 7C to determine numerous other pulse parameters. In addition to determining a pulse rate, CI, and PVI, the pulse processor 520A can, for instance, detect blood pressure changes. Such parameter information can be useful for determining appropriate doses or timings for delivery of medicine to an individual or designing an intelligent cuff inflation system for measuring patient blood pressure. Moreover, in certain embodiments, advantageously the parameter information can be based on a carotid signal sensed closer to an individual's heart and with fewer turns in vasculature than a signal sensed from the individual's wrist or finger, and thus can be useable to determine relatively reliable or accurate parameter information.

The collection processing module 430 can receive the pulse rate and related pulse parameters from the acoustic signal processor 410. The probe error detection module 430B of the collection processing module 430 can use the parameters, for example, to determine a sensor or probe connection state including a probe-off, probe-error, or probe-on state, such as discussed with respect to FIG. 9. Further, the collection processing module 430 can use the pulse rate and other pulse parameters and available information to determine a pulse wave transit time (PWTT), corresponding to the blood pressure of an individual. Advantageously, in certain embodiments, by using the filtered acoustic signal 740 and another signal from an acoustic sensor near an individual's heart, PWTT can be determined with greater robustness and accuracy than using some other methods. The filtered acoustic signal 740 and the signal from the another sensor can provide signals in the fluid domain that may not introduce domain conversion delay. For instance, if PWTT may be determined using an ECG signal, the determined PWTT value can include a domain transition delay time for a bodily electrical signal to transfer to the individual's muscles.

Figure 7D:
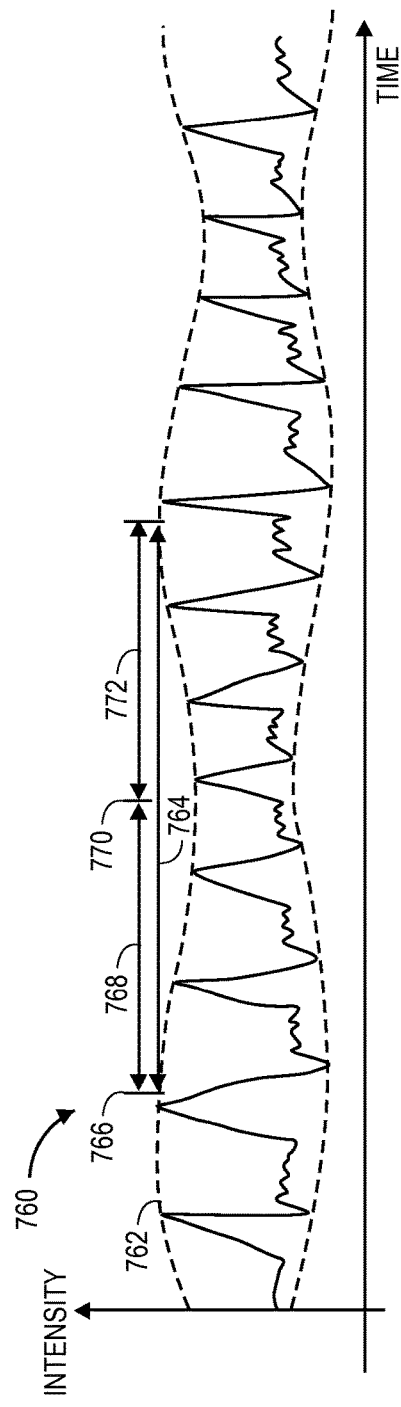
FIG. 7D is an example filtered acoustic signal generated by a filter that illustrates amplitude modulation.

FIG. 7D is a filtered acoustic signal 760 that illustrates amplitude modulation. Inhalation and exhalation can create positive pressure and negative pressure, respectively, on an individual's blood vessels, which may modulate the individual's pulse signal. Under certain conditions, an individual's respiration can amplitude modulate ("AM") 762 an acoustic signal, such as filtered acoustic signal 720 of FIG. 7B, sensed from the neck of the individual. In particular, the modulation period 764 can be inversely related to the individual's respiration rate. Certain implementations may utilize other modulations of the acoustic signal, such as a frequency modulation, to determine the respiration rate in place of or in addition to amplitude modulation.

In some embodiments, respiration rate can be determined in the frequency domain by analyzing the spectrum of the filtered acoustic signal 760. In the frequency domain, the filtered acoustic signal 760 can include at least a peak corresponding to the pulse rate and two respiration peak sidebands, displaced on either side of the pulse rate peak. By extracting the respiration beak sidebands, the respiration rate corresponding to the two respiration peaks can be determined.

In some embodiments, respiration rate can be determined in the time domain based on the respiration modulation period 764. A time domain calculation may be based upon envelope detection of the filtered acoustic signal 760, such as a curve-fit to the peaks (or valleys) of the filtered acoustic signal 760 or, alternatively, the peak-to-peak variation. Related measurements of variation in a plethysmograph envelope are described, for instance, in U.S. patent application Ser. No. 11/952,940, filed Dec. 7, 2007, which is incorporated by reference in its entirety herein.

In some embodiments, the respiration processor 520B of FIG. 5 can determine local maxima 766 and minima 770 in the upper envelope 762 of the filtered acoustic signal 760. The maxima 766 and minima 770 can correspond to, or may be further processed to determine, various respiratory events, such as the onset of inspiration Ti 766, the onset of expiration Te 770, the duration of inspiration Tie 768, the duration of expiration Tei 772, the ratio of the duration of inspiration to expiration Tie/Tei, the ratio of the duration of expiration to inspiration Tei/Tie, respiration rate, or other respiration-related events.

Figure 8:
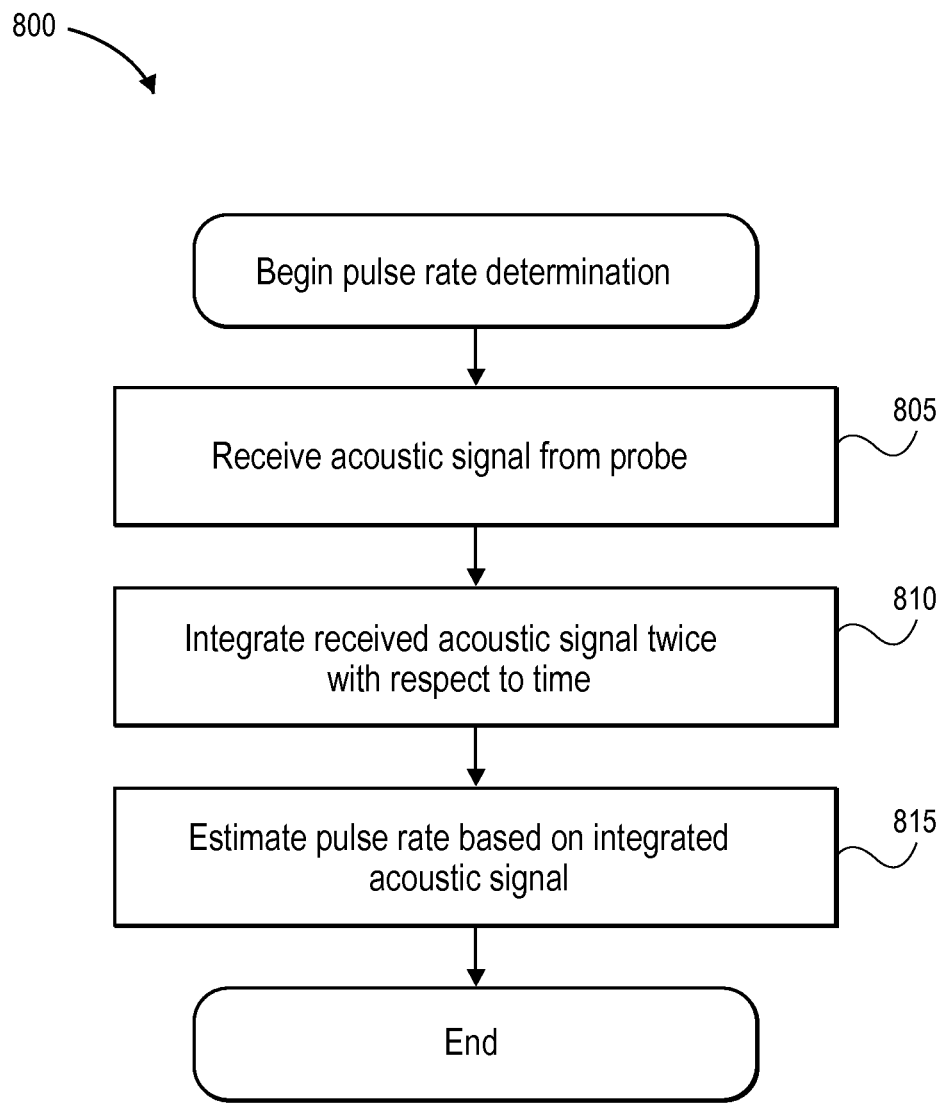
FIG. 8 illustrates a process for determining a patient pulse rate based on an acoustic signal.

FIG. 8 illustrates a process 800 for determining a patient pulse rate based on an acoustic signal, such as the acoustic signal 700 of FIG. 7A. For convenience, the process 800 is described in the context of the signals, systems, and devices of FIGS. 2A-B, 3-6, and 7A-D, but may instead be implemented by other signals, systems, and devices described herein or other computing systems.

At block 805, an acoustic signal can be received from a probe. The acoustic signal can be a signal obtained from the neck of a patient via the probe, such as the first acoustic sensor 210 of FIGS. 2A-B or the sensor head 306 of FIG. 3. The acoustic signal 412 can correspond to a signal received from the A/D converter 331 by the DSP 340 of FIG. 3 or the acoustic signal 412 received by the acoustic signal processor 410 of FIGS. 4 and 5.

At block 810, the received acoustic signal can be integrated twice with respect to time. The integration can be performed by the DSP 340 or the acoustic filter 510 of FIGS. 5 and 6. In some embodiments, the integration can be performed by the acoustic filter 510 in the frequency domain as discussed with respect to FIG. 6.

At block 815, a pulse rate can be estimated based on the integrated acoustic signal. The DSP 340 or acoustic signal processor 410 can estimate the pulse rate based on the reciprocal of the time period between pulses of the integrated acoustic signal, such as time period 748 of FIG. 7C.

Although block 810 can include the operation of integrating the received acoustic signal twice with respect to time in some embodiments, the operation at block 810 can include one or more other filtering operations (for example, differentiating, integrating, multiplying, subtracting, or computing the results of another function) in other embodiments to reverse or undue changes to the received acoustic signal due to the probe, as well as one or more associated processing modules.

Figure 9:
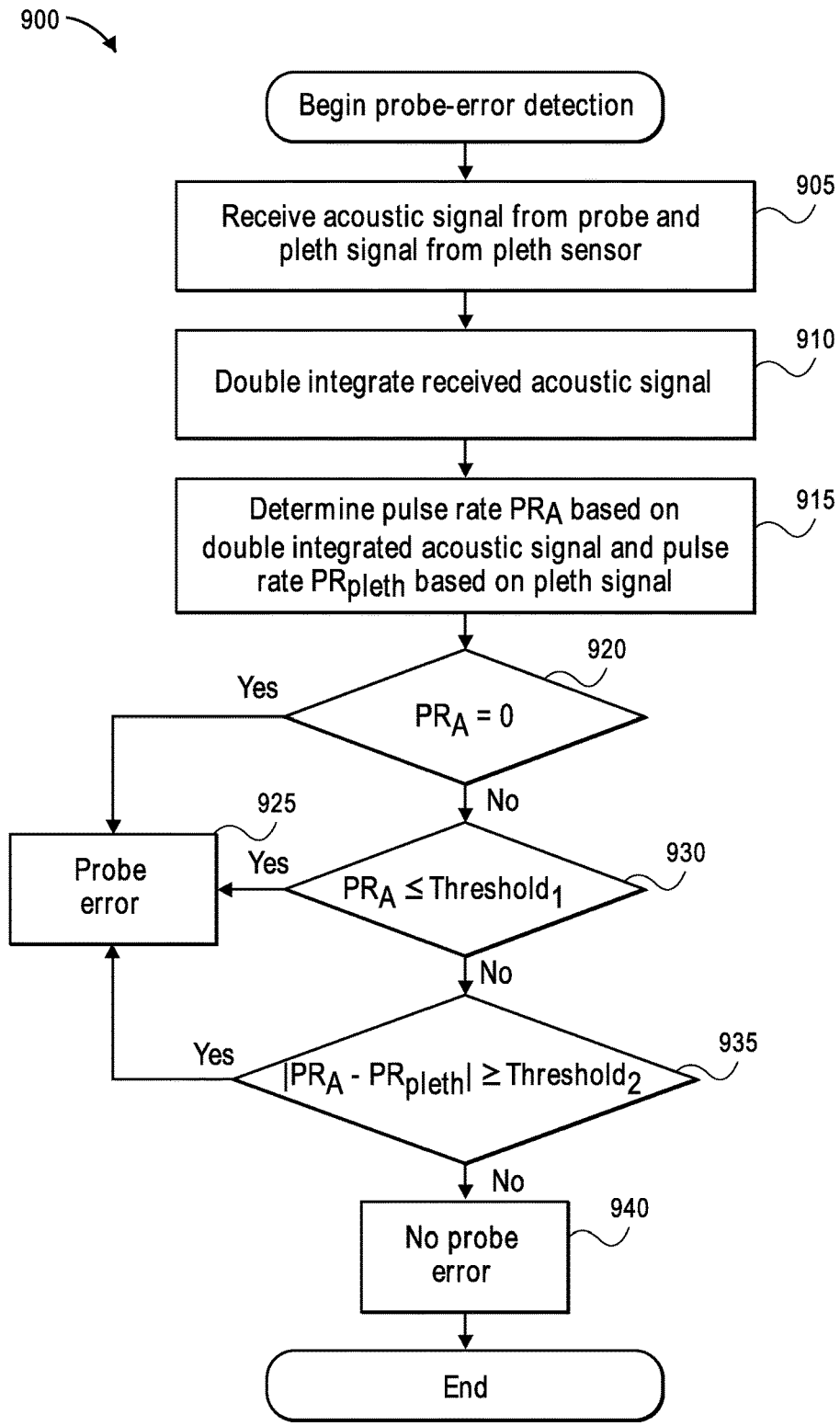
FIG. 9 illustrates a process for detecting an acoustic probe error.

FIG. 9 illustrates a process 900 for detecting an acoustic probe error. For convenience, the process 900 is described in the context of the signals, systems, and devices of FIGS. 2A-B, 3-5, and 7A-D, but may instead be implemented by other signals, systems, and devices described herein or other computing systems.

At block 905, an acoustic signal can be received from a probe, and a plethysmograph signal can be received from a pleth sensor. The acoustic signal can be a signal obtained from the neck of a patient via the probe, such as the first acoustic sensor 210 of FIGS. 2A-B or the sensor head 306 of FIG. 3. The acoustic signal 412 can correspond to a signal received from the A/D converter 331 by the DSP 340 of FIG. 3 or the acoustic signal 412 received by the acoustic signal processor 410 of FIGS. 4 and 5. The plethysmograph signal can be a signal obtained from the finger of a patient via a non-invasive sensor, such as the plethysmograph sensor 230 of FIG. 2B or optical sensor 302 of FIG. 3. The plethysmographic signal can correspond to a signal received from the A/D converter 335 by the DSP 340 of FIG. 3 or the plethysmograph signal 422 received by the plethysmograph processor 420 of FIG. 4.

At block 910, the received acoustic signal can be integrated twice with respect to time. The integration can be performed by the DSP 340 or the acoustic filter 510 of FIGS. 5 and 6. In some embodiments, the integration can be performed by the acoustic filter 510 in the frequency domain as discussed with respect to FIG. 6.

At block 915, a pulse rate can be estimated based on the integrated acoustic signal and the plethysmograph signal. The DSP 340 or acoustic signal processor 410 can estimate the pulse rate $PR_A$ based on the reciprocal of the time period between pulses of the integrated acoustic signal, such as time period 748 of FIG. 7C. The DSP 340 or plethysmograph signal processor 420 can estimate the pulse rate $PR_{pleth}$ using the plethysmograph processor 422.

At block 920, the pulse rate $PR_A$ can be compared to a pulse rate value of zero or about zero beats per minute. The DSP 340 or probe error detection module 430B can perform the comparison. In response to determining that the pulse rate equals zero or about zero, at block 925, the DSP 340 or combining module 430 can activate an alarm condition indicating a probe error. For instance, the DSP 340 can transmit a signal to the instrument manager 350 of FIG. 3 to activate an alarm 366 of one of the I/O devices 360.

At block 930, the pulse rate $PR_A$ can be compared to a first threshold pulse rate value. The DSP 340 or probe error detection module 430B can perform the comparison. The first threshold value can be a value determined based on a minimum pulse rate that would be expected for an individual. In some embodiments, the first threshold can equal 20 beats per minute. In response to determining that the pulse rate does not exceed the first threshold, at block 925, the DSP 340 or combining module 430 can activate an alarm condition indicating a probe error. For instance, the DSP 340 can transmit a signal to the instrument manager 350 to activate an alarm 366 of one of the I/O devices 360.

At block 935, the difference between the pulse rate $PR_A$ and pulse rate $PR_{pleth}$ can be compared to a second threshold pulse rate value. The second threshold value can be a value determined based on a minimum pulse rate difference that would be expected between an acoustic and plethysomographic determined pulse rate. In some embodiments, the second threshold can equal 5 or 10 beats per minute. In response to determining that the difference exceeds or equals the second threshold, at block 925, the DSP 340 or combining module 430 can activate an alarm condition indicating a probe error. For instance, the DSP 340 can transmit a signal to the instrument manager 350 to activate an alarm 366 of one of the I/O devices 360.

At block 940, a no-probe-error state can be determined. For instance, the DSP 340 or combining module 430 can determine that probe may be operating without error and may take no corrective action. In some embodiments, the DSP 340 or combining module 430 can utilize the absence of a probe error to determine the validity of a pulse rate or to cause DSP 340 or combining module 430 to output a particular value for display to a patient.

In some embodiments, other approaches can be additionally or alternatively used to determine probe errors or activate alarms based on the integrated acoustic signal. For instance, the timing or shape of features of the integrated acoustic signal can be compared to features of one or more other signals, such as signals from a plethysomographic sensor or another acoustic sensor. The features can include local maxima or minima of the signals, and the like. Deviations in the timing or shape between features of the integrated acoustic signal and features of the other signals can indicate a probe error or alarm condition. As another example, detected energy levels in lower frequencies of the integrated acoustic signal can be used to determine the presence of a pulse rate and thus to indicate a no probe error state. In a further example, the integrated acoustic signal can be compared to one or more signal templates to determine whether the integrated acoustic signal has an expected form. When the integrated acoustic signal does not have an expected form, a probe error indication can be triggered and an alarm can be activated. Such other approaches are described in more detail in U.S. patent application Ser. No. 14/137,629, filed Dec. 20, 2013, which is incorporated by reference in its entirety herein.

Although block 910 can include the operation of integrating the received acoustic signal twice with respect to time in some embodiments, the operation at block 910 can include one or more other filtering operations (for example, differentiating, integrating, multiplying, subtracting, or computing the results of another function) in other embodiments to reverse or undue changes to the received acoustic signal due to the probe, as well as one or more associated processing modules.

Figure 10:
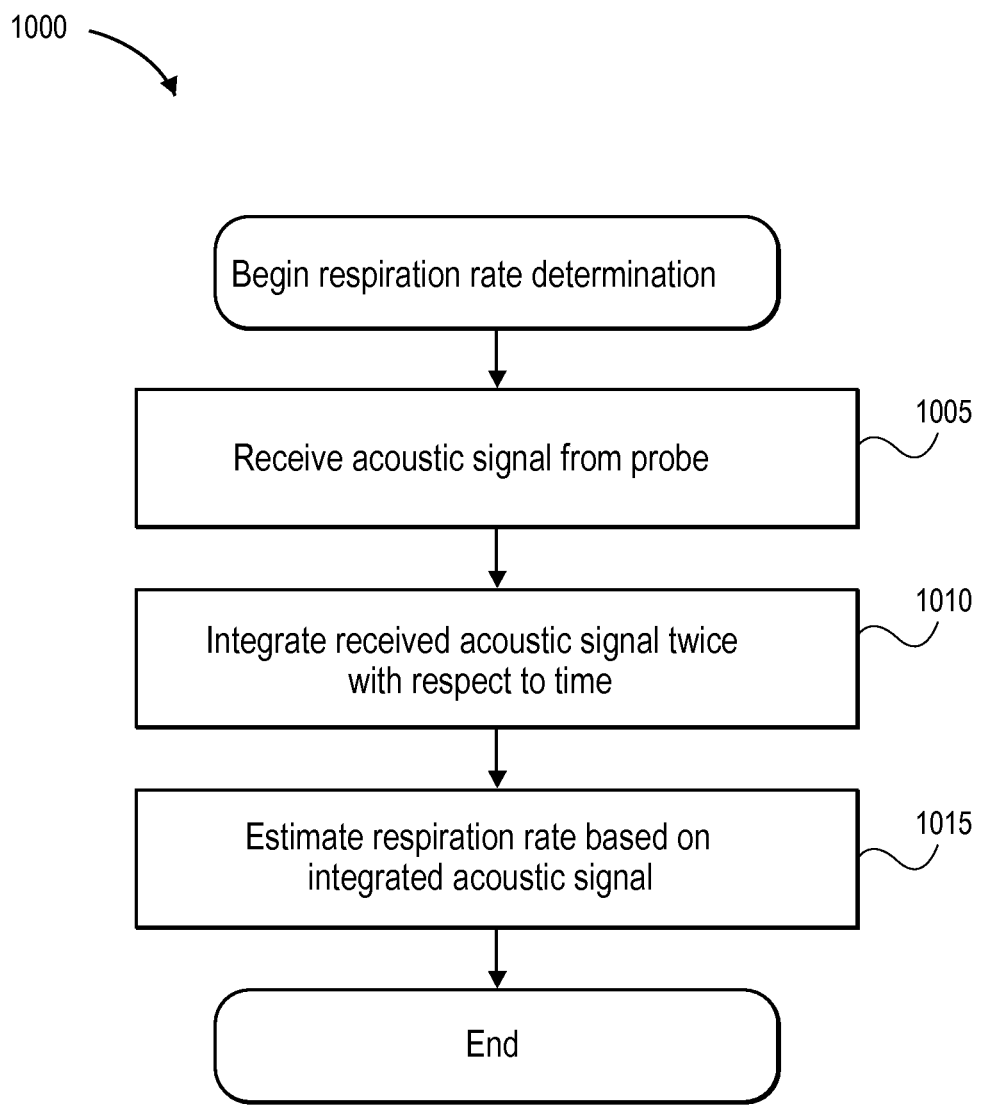
FIG. 10 illustrates a process for determining a patient respiration rate based on an acoustic signal.

FIG. 10 illustrates a process 1000 for determining a patient respiration rate based on an acoustic signal, such as the acoustic signal 700 of FIG. 7A. For convenience, the process 1000 is described in the context of the signals, systems, and devices of FIGS. 2A-B, 3-5, and 7A-D, but may instead be implemented by other signals, systems, and devices described herein or other computing systems.

At block 1005, the acoustic signal can be received from a probe. The acoustic signal can be a signal obtained from the neck of a patient via the probe, such as the first acoustic sensor 210 of FIGS. 2A-B or the sensor head 306 of FIG. 3. The acoustic signal 412 can correspond to a signal received from the A/D converter 331 by the DSP 340 of FIG. 3 or the acoustic signal 412 received by the acoustic signal processor 410 of FIGS. 4 and 5.

At block 1010, the received acoustic signal can be integrated twice with respect to time. The integration can be performed by the DSP 340 or the acoustic filter 510 of FIGS. 5 and 6. In some embodiments, the integration can be performed by the acoustic filter 510 in the frequency domain as discussed with respect to FIG. 6.

At block 1015, a respiration rate can be estimated based on the integrated acoustic signal. For instance, the DSP 340 or acoustic signal processor 410 can estimate the respiration rate based on amplitude modulation of the integrated acoustic signal as discussed with respect to FIG. 7D.

Although block 1010 can include the operation of integrating the received acoustic signal twice with respect to time in some embodiments, the operation at block 1010 can include one or more other filtering operations (for example, differentiating, integrating, multiplying, subtracting, or computing the results of another function) in other embodiments to reverse or undue changes to the received acoustic signal due to the probe, as well as one or more associated processing modules.

Figure 11:
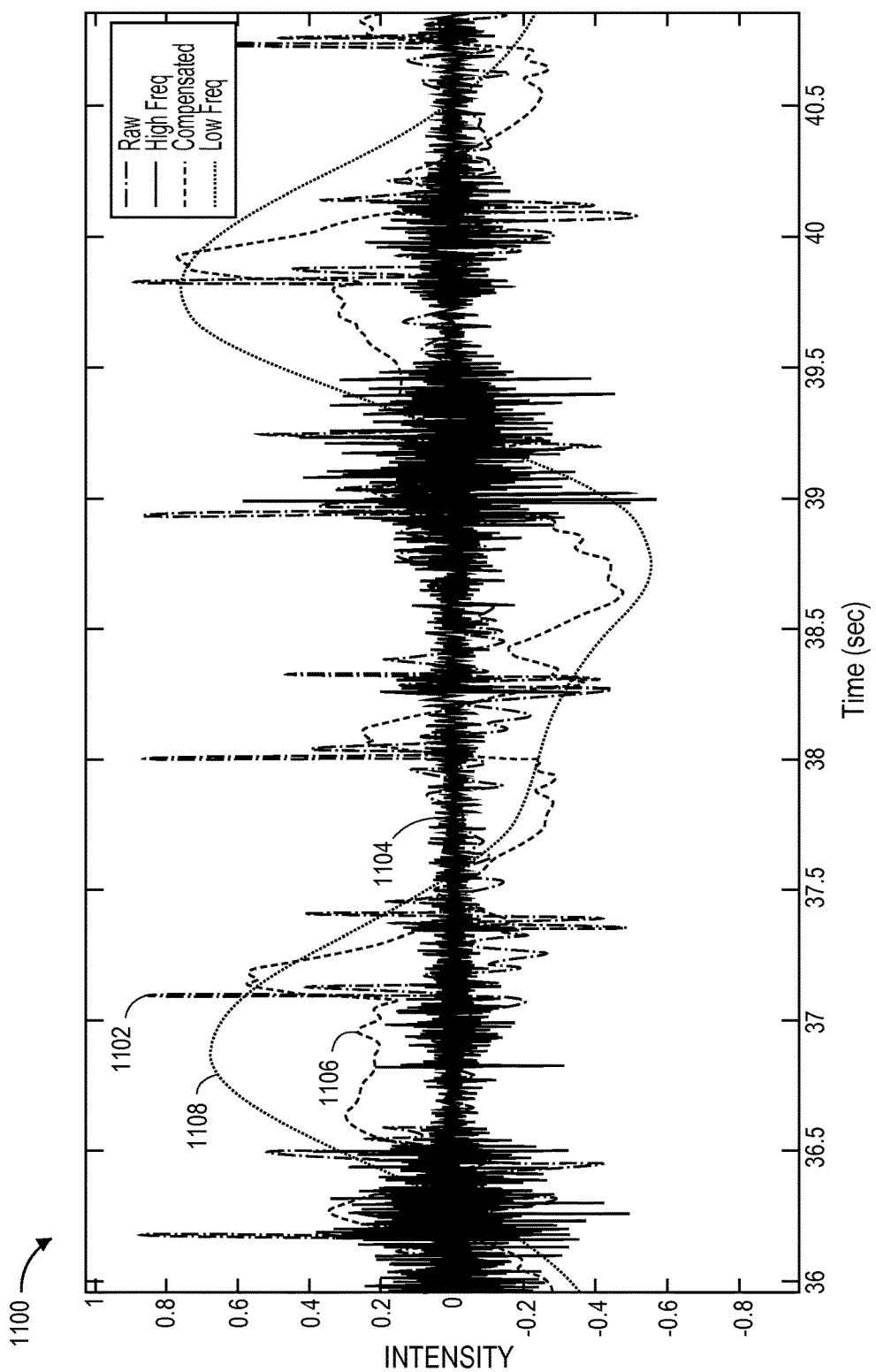
FIG. 11 illustrates example signals processed by an acoustic signal processor.

FIG. 11 illustrates example signals processed by an acoustic signal processor. The signals include a raw acoustic signal 1102, such as the acoustic signal 412 of FIGS. 4-6, processed by the acoustic signal processor 410 of FIGS. 4 and 5. The raw acoustic signal 1102 can be sensed from the neck of a patient via an acoustic sensor, such as the first acoustic sensor 210 of FIGS. 2A-B or the sensor head 306 of FIG. 3. The acoustic signal 1102 is shown plotted on an intensity axis versus a time axis. As can be seen in FIG. 11, the acoustic signal 1102 can be a relatively chaotic signal, including numerous frequency components ranging from low to high frequency components.

The signals of FIG. 11 further include a compensated acoustic signal 1106 that can be a filtered acoustic signal generated by a filter, such as the acoustic filter 510 of FIGS. 5 and 6. In one implementation, the raw acoustic signal 1102 may have been integrated twice with respect to time to generate the compensated acoustic signal 1106. As can be seen, the compensated acoustic signal 1106 can be a relatively ordered signal, including fewer frequency components than the raw acoustic signal 1102.

In addition, the signals of FIG. 11 include a high frequency acoustic signal 1104 and a low frequency acoustic signal 1108. The high frequency acoustic signal 1104 can illustrate just the high frequency components of the compensated acoustic signal 1106, and the low frequency acoustic signal 1108 can just illustrate the low frequency components of the compensated acoustic signal 1106 (for example, the low frequency components between about 0.2 Hz and 0.8 Hz).

Advantageously, in certain embodiments, the low frequency acoustic signal 1108 can be used to accurately and precisely determine one or more respiration parameters for a patient since the local maxima and minima of the low frequency acoustic signal 1108 can directly correspond to exhalation and inhalation. Multiple consecutive local maxima or multiple consecutive local minima can thus be correctly identified as multiple exhalations or multiple inhalations. As a result, an acoustic signal processor can, for example, determine a time when inspiration or expiration begin (Ti or Te, respectively), a time duration of an inspiration or an expiration (Tie or Tei, respectively), a ratio of the time duration of inspiration to expiration, or of expiration to inspiration (Tie/Tei or Tei/Tie, respectively) with greater confidence.

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A physiological monitoring system configured to noninvasively detect acoustic vibrations indicative of one or more physiological parameters of a medical patient, the physiological monitoring system comprising:
an acoustic sensor associated with a transfer function, the transfer function indicative of a transform caused by at least one of processing circuitry of the acoustic sensor or a piezoelectric membrane of the acoustic sensor, wherein the acoustic sensor is configured to be attached to a medical patient, detect acoustic vibrations associated with the medical patient, and generate a patient signal indicative of the acoustic vibrations, wherein the transfer function of the acoustic sensor has an effect on the patient signal such that the patient signal can be modeled as a derivative with respect to time of a signal indicative of the acoustic vibrations;
a memory configured to store the transfer function of the acoustic sensor; and
a processor in communication with the acoustic sensor and the memory, and configured to:
retrieve, from the memory, the transfer function of the acoustic sensor,
determine the transfer function of the acoustic sensor based at least in part on the transfer function of the acoustic sensor,
deconvolve the patient signal using the transfer function of the acoustic sensor to lessen the effect of the transfer function on the patient signal to generate a deconvolved patient signal indicative of the acoustic vibrations,
estimate a physiological parameter of the medical patient based at least in part on the deconvolved patient signal, wherein the physiological parameter includes at least one of a respiratory parameter or a cardiac parameter, and
output an indication of the estimated physiological parameter for presentation to a care giver.

2. The physiological monitoring system of claim 1, wherein local maxima of the deconvolved patient signal correspond to peak expansions of skin of the medical patient, and local minima of the deconvolved patient signal correspond to peak contractions of the skin of the medical patient.

3. The physiological monitoring system of claim 1, wherein the acoustic sensor is operatively coupled to a neck of the medical patient when detecting the acoustic vibrations associated with the medical patient.

4. The physiological monitoring system of claim 1, wherein the physiological parameter comprises a pulse rate and wherein the processor is configured to estimate the pulse rate based at least in part on a time period between at least one of one or more peaks of the deconvolved patient signal or one or more valleys of the deconvolved patient signal.

5. The physiological monitoring system of claim 1, wherein the processor is configured to activate an alarm based at least in part on the estimated physiological parameter.

6. The physiological monitoring system of claim 5, wherein the processor is configured to activate the alarm based at least in part on the estimated physiological parameter and a physiological parameter of the medical patient determined based at least in part on a signal from a different sensor attached to the medical patient.

7. The physiological monitoring system of claim 6, wherein the different sensor comprises a plethysmograph sensor.

8. The physiological monitoring system of claim 1, wherein the physiological parameter includes at least one of respiration rate, pulse rate, expiratory flow, tidal volume, minute volume, apnea duration, breath sounds, rales, rhonchi, stridor, air volume, airflow, heart sounds, or change in heart sounds.

9. The physiological monitoring system of claim 1, wherein at least a portion of the effect of the transfer function is a result of the processing circuitry of the acoustic sensor.

10. The physiological monitoring system of claim 1, wherein at least a portion of the effect of the transfer function is a result of a sensed motion of skin of the medical patient during sensing by the acoustic sensor.

11. The physiological monitoring system of claim 1, wherein at least a portion of the effect of the transfer function is a result of the piezoelectric membrane of the acoustic sensor.

12. The physiological monitoring system of claim 1, wherein to deconvolve the patient signal, the processor is configured to apply a Fourier transform to the patient signal.

13. A method of determining values indicative of one or more physiological parameters of a medical patient, the method comprising:
receiving a patient signal from an acoustic sensor attached to a medical patient, wherein the acoustic sensor is associated with a transfer function indicative of a transform caused by at least one of processing circuitry of the acoustic sensor or a piezoelectric membrane of the acoustic sensor, wherein the acoustic sensor is configured to detect acoustic vibrations associated with the medical patient and generate the patient signal, wherein the patient signal is indicative of the acoustic vibrations, wherein the transfer function of the acoustic sensor has an effect on the patient signal such that the patient signal can be modeled as a derivative with respect to time of a signal indicative of the acoustic vibrations,
retrieving, from memory, the transfer function of the acoustic sensor;
deconvolving the patient signal using the transfer function of the acoustic sensor to diminish the effect of the transfer function on the patient signal to generate a deconvolved patient signal indicative of the acoustic vibrations;
estimating, using a processor, a physiological parameter of the medical patient based at least in part on the deconvolved patient signal, wherein the physiological parameter includes at least one of a respiratory parameter or a cardiac parameter; and
outputting an indication of the estimated physiological parameter for presentation to a care giver.

14. The method of claim 13, wherein the physiological parameter comprises at least one of respiration rate, pulse rate, expiratory flow, tidal volume, minute volume, apnea duration, breath sounds, rales, rhonchi, stridor, air volume, airflow, heart sounds, or change in heart sounds.

15. The method of claim 13, wherein at least a portion of the effect of the transfer function is a result of the processing circuitry of the acoustic sensor.

16. The method of claim 13, wherein at least a portion of the effect of the transfer function is a result of a sensed motion of skin of the medical patient during operation of the acoustic sensor.

17. The method of claim 13, wherein at least a portion of the effect of the transfer function is a result of the piezoelectric membrane of the acoustic sensor.

18. The physiological monitoring system of claim 1, wherein to deconvolve the patient signal, the processor is configured to double integrate the patient signal with respect to time.

19. The method of claim 13, wherein said deconvolving the patient signal comprises double integrating the patient signal with respect to time.

20. The method of claim 13, wherein said deconvolving the patient signal comprises applying a Fourier transform to the patient signal.

* * * * *